United States Patent
Maheshwari et al.

(10) Patent No.: US 11,779,544 B1
(45) Date of Patent: *Oct. 10, 2023

(54) ANTITHROMBOTIC NANOPARTICLES AND METHODS FOR TREATING NECROTIZING ENTEROCOLITIS

(71) Applicant: University of South Florida, Tampa, FL (US)

(72) Inventors: Akhil Maheshwari, Clarksville, MD (US); Samuel Wickline, Temple Terrace, FL (US); Kopperuncholan Namachivayam, Cockeyesville, MD (US); Hua Pan, Tampa, FL (US)

(73) Assignee: University of South Florida, Tampa, FL (US)

( * ) Notice: Subject to any disclaimer, the term of this patent is extended or adjusted under 35 U.S.C. 154(b) by 215 days.

This patent is subject to a terminal disclaimer.

(21) Appl. No.: 17/215,668

(22) Filed: Mar. 29, 2021

Related U.S. Application Data

(63) Continuation of application No. 16/593,435, filed on Oct. 4, 2019, now Pat. No. 10,987,315.

(60) Provisional application No. 62/775,240, filed on Dec. 4, 2018.

(51) Int. Cl.
| | | |
|---|---|---|
| *A61K 9/51* | (2006.01) | |
| *A61K 47/69* | (2017.01) | |
| *A61K 31/401* | (2006.01) | |
| *A61K 38/17* | (2006.01) | |
| *A61P 1/00* | (2006.01) | |
| *A61K 45/06* | (2006.01) | |

(52) U.S. Cl.
CPC .......... *A61K 9/5123* (2013.01); *A61K 31/401* (2013.01); *A61K 38/1767* (2013.01); *A61K 45/06* (2013.01); *A61K 47/6929* (2017.08); *A61P 1/00* (2018.01)

(58) Field of Classification Search
CPC ........ A61K 9/51; A61K 47/69; A61K 31/401; A61K 38/17; A61K 45/06; A61P 1/00
See application file for complete search history.

(56) References Cited

U.S. PATENT DOCUMENTS

| | | |
|---|---|---|
| 5,578,325 A | 11/1996 | Domb et al. |
| 5,690,907 A | 11/1997 | Lanza et al. |
| 5,780,010 A | 7/1998 | Lanza et al. |
| 5,958,371 A | 9/1999 | Lanza et al. |
| 5,989,520 A | 11/1999 | Lanza et al. |
| 6,007,845 A | 12/1999 | Domb et al. |
| 9,415,018 B2 | 8/2016 | Wickline et al. |
| 9,764,043 B2 * | 9/2017 | Myerson ............ A61K 47/6909 |
| 9,808,500 B2 | 11/2017 | Wickline et al. |
| 2013/0064765 A1 | 3/2013 | Myerson et al. |
| 2015/0011578 A1 | 1/2015 | Wickline et al. |
| 2015/0335623 A1 | 11/2015 | Wickline et al. |
| 2016/0324835 A1 | 11/2016 | Wickline et al. |
| 2017/0065669 A1 | 3/2017 | Wickline et al. |
| 2017/0096451 A1 * | 4/2017 | Alkan ....................... A61P 3/00 |

FOREIGN PATENT DOCUMENTS

| | | |
|---|---|---|
| EP | 2512452 | 12/2010 |
| WO | 2011084700 | 7/2011 |

OTHER PUBLICATIONS

Yamasoto. Case Based Pediatrics For Students and Residents (2002).*
Aatonen MT, Ohman T, Nyman TA, Laitinen S, Gronholm M, Siljander PR. Isolation and characterization of platelet-derived extracellular vesicles. J Extracell Vesicles. 2014;3.
Baer VL, Henry E, Lambert DK, et al. Implementing a program to improve compliance with neonatal intensive care unit transfusion guidelines was accompanied by a reduction in transfusion rate: a pre-post analysis within a multihospital health care system. Transfusion. 2011;51(2):264-269.
Baer VL, Lambert DK, Henry E, Christensen RD. Severe Thrombocytopenia in the NICU. Pediatrics. 2009;124(6):e1095-1100.
Baer VL, Lambert DK, Henry E, Snow GL, Sola-Visner MC, Christensen RD. Do platelet transfusions in the NICU adversely affect survival? Analysis of 1600 thrombocytopenic neonates in a multihospital healthcare system. J Perinatol. 2007;27(12):790-796.
Bergmeier W, Schulte V, Brockhoff G, Bier U, Zirngibl H, Nieswandt B. Flow cytometric detection of activated mouse integrin alphaIIb-beta3 with a novel monoclonal antibody. Cytometry. 2002;48(2):80-86.
Brummel KE, Paradis SG, Butenas S, Mann KG. Thrombin functions during tissue factor-induced blood coagulation. Blood. 2002;100(1):148-152.
Buck ML. Bivalirudin as an Alternative to Heparin for Anticoagulation in Infants and Children. J Pediatr Pharmacol Ther. 2015;20(6):408-417.
Chen J, Lanza GM, Wickline SA. Quantitative magnetic resonance fluorine imaging: today and tomorrow. Wiley Interdiscip Rev Nanomed Nanobiotechnol. 2010;2(4):431-440.
Chen J, Vemuri C, Palekar RU, et al. Antithrombin nanoparticles improve kidney reperfusion and protect kidney function after ischemia-reperfusion injury. Am J Physiol Renal Physiol. 2015;308(7):F765-773.
Christensen, Robert D., Erick Henry, and Antonio Del Vecchio. "Thrombocytosis and thrombocytopenia in the NICU: incidence, mechanisms and treatments." The Journal of Maternal-Fetal & Neonatal Medicine 25.sup4 (2012): 7-9.
Christensen RD, Henry E, Wiedmeier SE, et al. Thrombocytopenia among extremely low birth weight neonates: data from a multihospital healthcare system. J Perinatol. 2006;26(6):348-353.
Collins CE, Cahill MR, Newland AC, Rampton DS. Platelets circulate in an activated state in inflammatory bowel disease. Gastroenterology. 1994;106(4):840-845.
Cremer M, Sola-Visner M, Roll S, et al. Platelet transfusions in neonates: practices in the United States vary significantly from those in Austria, Germany, and Switzerland. Transfusion. 2011;51(12):2634-2641.

(Continued)

*Primary Examiner* — Shirley V Gembeh
(74) *Attorney, Agent, or Firm* — Meunier Carlin & Curfman LLC

(57) ABSTRACT

The present disclosure is directed to antithrombotic nanoparticles and methods of treating necrotizing enterocolitis.

17 Claims, 14 Drawing Sheets

Specification includes a Sequence Listing.

(56) References Cited

OTHER PUBLICATIONS

Curley A, Stanworth SJ, Willoughby K, et al. Randomized Trial of Platelet-Transfusion Thresholds in Neonates. N Engl J Med. 2018, 242-251.
Deutschmann A, Schlagenhauf A, Leschnik B, Hoffmann KM, Hauer A, Muntean W. Increased procoagulant function of microparticles in pediatric inflammatory bowel disease: role in increased thrombin generation. J Pediatr Gastroenterol Nutr. 2013;56(4):401-407.
Drake TA, Morrissey JH, Edgington TS. Selective cellular expression of tissue factor in human tissues. Implications for disorders of hemostasis and thrombosis. Am J Pathol. 1989;134(5):1087-1097.
Garcia MG, Duenas E, Sola MC, Hutson AD, Theriaque D, Christensen RD. Epidemiologic and outcome studies of patients who received platelet transfusions in the neonatal intensive care unit. J Perinatol. 2001;21(7):415-420.
Gerday E, Baer VL, Lambert DK, et al. Testing platelet mass versus platelet count to guide platelet transfusions in the neonatal intensive care unit. Transfusion. 2009;49(10):2034-2039.
Gladwell TD. Bivalirudin: a direct thrombin inhibitor. Clin Ther. 2002;24(1):38-58.
Golino P. The inhibitors of the tissue factor:factor VII pathway. Thromb Res. 2002;106(3):V257-265.
Gomez-Outes A, Suarez-Gea ML, Lecumberri R, Rocha E, Pozo-Hernandez C, Vargas-Castrillon E. New parenteral anticoagulants in development. Ther Adv Cardiovasc Dis. 2011;5(1):33-59.
Hutter JJ, Jr., Hathaway WE, Wayne ER. Hematologic abnormalities in severe neonatal necrotizing enterocolitis. J Pediatr. 1976;88(6):1026-1031.
Josephson CD, Su LL, Christensen RD, et al. Platelet transfusion practices among neonatologists in the United States and Canada: results of a survey. Pediatrics. 2009;123(1):278-285.
Kenton AB, Hegemier S, Smith EO, et al. Platelet transfusions in infants with necrotizing enterocolitis do not lower mortality but may increase morbidity. J Perinatol. 2005;25(3):173-177.
Kling PJ, Hutter JJ. Hematologic abnormalities in severe neonatal necrotizing enterocolitis: 25 years later. J Perinatol. 2003;23(7):523-530.
Liu ZJ, Hoffmeister KM, Hu Z, et al. Expansion of the neonatal platelet mass is achieved via an extension of platelet lifespan. Blood. 2014;123(22):3381-3389.
Maheshwari A. Immunologic and Hematological Abnormalities in Necrotizing Enterocolitis. Clin Perinatol. 2015;42(3):567-585.
Manco-Johnson MJ. Neonatal antithrombin III deficiency. Am J Med. 1989;87(3B):49S-52S.
Mathiowitz, E., and R. Langer. Polyanhydride microspheres as drug carriers I. Hot-melt microencapsulation. Journal of controlled release 5.1 (1987): 13-22.
Mathiowitz, E., M. D. Cohen, and R. Langer. "Novel microcapsules for delivery systems." Reactive Polymers, Ion Exchangers, Sorbents 6.2-3 (1987): 275-283.
Mathiowitz, Edith, et al. "Polyanhydride microspheres as drug carriers. II. Microencapsulation by solvent removal." Journal of Applied Polymer Science 35.3 (1988): 755-774.
MohanKumar K, Kaza N, Jagadeeswaran R, et al. Gut mucosal injury in neonates is marked by macrophage infiltration in contrast to pleomorphic infiltrates in adult: evidence from an animal model. Am J Physiol Gastrointest Liver Physiol. 2012;303(1):G93-102.
MohanKumar K, Killingsworth CR, McIlwain RB, et al. Intestinal epithelial apoptosis initiates gut mucosal injury during extracorporeal membrane oxygenation in the newborn piglet. Lab Invest. 2014;94(2):150-160.
MohanKumar K, Namachivayam K, Chapalamadugu KC, et al. Smad7 Interrupts TGF-' Signaling in Intestinal Macrophages and Promotes Inflammatory Activation of these Cells during Necrotizing Enterocolitis. Pediatr Res. 2016;79(6):951-961.
MohanKumar K, Namachivayam K, Cheng F, et al. Trinitrobenzene Sulfonic Acid-induced Intestinal Injury in Neonatal Mice Activates Transcriptional Networks Similar to those seen in Human Necrotizing Enterocolitis. Pediatr Res. 2016;81(1):99-112.

Mull MM, Hathaway WE. Altered platelet function in newborns. Pediatr Res. 1970;4(3):229-237.
Murray, Christopher B., A. CR Kagan, and M. G. Bawendi. Synthesis and characterization of monodisperse nanocrystals and close-packed nanocrystal assemblies. Annual review of materials science 30.1 (2000): 545-610.
Myerson J, He L, Lanza G, Tollefsen D, Wickline S. Thrombin-inhibiting perfluorocarbon nanoparticles provide a novel strategy for the treatment and magnetic resonance imaging of acute thrombosis. J Thromb Haemost. 2011;9(7):1292-1300.
Namachivayam K, Blanco CL, MohanKumar K, et al. Smad7 inhibits autocrine expression of TGF-beta2 in intestinal epithelial cells in baboon necrotizing enterocolitis. Am J Physiol Gastrointest Liver Physiol. 2013;304(2):G167-180.
Namachivayam K, MohanKumar K, Garg L, Torres BA, Maheshwari A. Neonatal Mice with Necrotizing Enterocolitis-like Injury Develop Thrombocytopenia despite Increased Megakaryopoiesis. Pediatr Res. 2017;81:817-824.
Neu J, Walker WA. Necrotizing enterocolitis. N Engl J Med. 2011;364(3):255-264.
Ng PC. Biomarkers of necrotising enterocolitis. Semin Fetal Neonatal Med. 2014;19(1):33-38.
Nickel RS, Josephson CD. Neonatal Transfusion Medicine: Five Major Unanswered Research Questions for the Twenty-First Century. Clin Perinatol. 2015;42(3):499-513.
Nielsen MH, Beck-Nielsen H, Andersen MN, Handberg A. A flow cytometric method for characterization of circulating cell-derived microparticles in plasma. J Extracell Vesicles. 2014;3.
Novak EK, Sweet HO, Prochazka M, et al. Cocoa: a new mouse model for platelet storage pool deficiency. Br J Haematol. 1988;69(3):371-378.
O'Keeffe D, Olson ST, Gasiunas N, Gallagher J, Baglin TP, Huntington JA. The heparin binding properties of heparin cofactor II suggest an antithrombin-like activation mechanism. J Biol Chem. 2004;279(48):50267-50273.
Paolicelli et al., Surface-modified PLGA-based Nanoparticles that can Efficiently Associate and Deliver Virus-like Particles Nanomedicine. 5(6):843-853 (2010).
Pammi M, Cope J, Tarr PI, et al. Intestinal dysbiosis in preterm infants preceding necrotizing enterocolitis: a systematic review and meta-analysis. Microbiome. 2017;5(1):31.
Patel CC. Hematologic abnormalities in acute necrotizing enterocolitis. Pediatr Clin North Am. 1977;24(3):579-584.
Patel RM, Kandefer S, Walsh MC, et al. Causes and timing of death in extremely premature infants from 2000 through 2011. N Engl J Med. 2015;372(4):331-340.
Pellegrino, Teresa, et al. On the development of colloidal nanoparticles towards multifunctional structures and their possible use for biological applications. small 1.1 (2005): 48-63.
Remon JI, et al. Depth of bacterial invasion in resected intestinal tissue predicts mortality in surgical necrotizing enterocolitis. J Perinatol. 2015;35(9):755-62.
Saibeni S, Saladino V, Chantarangkul V, et al. Increased thrombin generation in inflammatory bowel diseases. Thromb Res. 2010;125(3):278-282.
Schmaier AH, Meloni FJ, Nawarawong W, Jiang YP. PPACK-thrombin is a noncompetitive inhibitor of alpha-thrombin binding to human platelets. Thromb Res. 1992;67(5):479-489.
Simak J, Holada K, Janota J, Stranak Z. Surface expression of major membrane glycoproteins on resting and TRAP-activated neonatal platelets. Pediatr Res. 1999;46(4):445-449.
Sorensen AL, Rumjantseva V, Nayeb-Hashemi S, et al. Role of sialic acid for platelet life span: exposure of beta-galactose results in the rapid clearance of platelets from the circulation by asialoglycoprotein receptor-expressing liver macrophages and hepatocytes. Blood. 2009;114(8):1645-1654.
Srinivas S, Watanabe T, Lin CS, et al. Cre reporter strains produced by targeted insertion of EYFP and ECFP into the ROSA26 locus. BMC Dev Biol. 2001; 1:4.
Stanworth SJ, Clarke P, Watts T, et al. Prospective, observational study of outcomes in neonates with severe thrombocytopenia. Pediatrics. 2009;124(5):e826-834.

(56) References Cited

OTHER PUBLICATIONS

Thomas MR, Storey RF. The role of platelets in inflammation. Thromb Haemost. 2015;114(3):449-458.

Tiedt R, Schomber T, Hao-Shen H, Skoda RC. Pf4-Cre transgenic mice allow the generation of lineage-restricted gene knockouts for studying megakaryocyte and platelet function in vivo. Blood. 2007;109(4):1503-1506.

Tollefsen DM. Heparin cofactor II deficiency. Arch Pathol Lab Med. 2002;126(11):1394-1400.

Trindade, Tito, Paul O'Brien, and Nigel L. Pickett. Nanocrystalline semiconductors: synthesis, properties, and perspectives. Chemistry of Materials 13.11 (2001): 3843-3858.

Ververidis M, Kiely EM, Spitz L, Drake DP, Eaton S, Pierro A. The clinical significance of thrombocytopenia in neonates with necrotizing enterocolitis. J Pediatr Surg. 2001;36(5):799-803.

Wall JE, Buijs-Wilts M, Arnold JT, et al. A flow cytometric assay using mepacrine for study of uptake and release of platelet dense granule contents. Br J Haematol. 1995;89(2):380-385.

Wickline SA, Neubauer AM, Winter P, Caruthers S, Lanza G. Applications of nanotechnology to atherosclerosis, thrombosis, and vascular biology. Arterioscler Thromb Vasc Biol. 2006;26(3):435-441.

Zelaya H, Rothmeier AS, Ruf W. Tissue factor at the crossroad of coagulation and cell signaling. J Thromb Haemost. 2018;16(10):1941-1952.

Zhang, L., et al., Nanoparticles in Medicine: Therapeutic Applications and Developments, Clin. Pharm. and Ther., 83(5):761-769, 2008.

Peter, Shawn D. St. et al., "The initial experience of antithrombin III in the management of neonates with necrotizing enterocolitis", Journal of Pediatric Surgery (2007), 42, pp. 704-708.

Kumral, Abdullah et al., "Activated protein C reduces intestinal injury in an experimental model of necrotizing enterocolitis", Journal of Pediatric Surgery (2010), 45, pp. 483-489.

Schoots, Ivo G., "Inhibition of coagulation and inflammation by activated protein C or antithrombin reduces intestinal ischemia/reperfusion injury in rats", Crit Care Med 2004 vol. 32, No. 6, pp. 1375-1382.

\* cited by examiner

ANTITHROMBOTIC NANOPARTICLES AND METHODS FOR TREATING NECROTIZING ENTEROCOLITIS

CROSS REFERENCE TO RELATED APPLICATIONS

This application is a continuation of U.S. application Ser. No. 16/593,435, filed Oct. 4, 2019, which claims the benefit of U.S. Provisional Patent Application Ser. No. 62/775,240 filed Dec. 4, 2018, the disclosure of which is expressly incorporated herein by reference.

STATEMENT REGARDING FEDERALLY SPONSORED RESEARCH

This invention was made with government support under Grant No. HL133022, HL073646, and DK102691 awarded by the National Institutes of Health. The government has certain rights in the invention.

FIELD

The present disclosure is directed to antithrombotic nanoparticles and methods of treating necrotizing enterocolitis.

BACKGROUND

Necrotizing enterocolitis (NEC) is an inflammatory bowel necrosis of premature infants, and is a leading cause of mortality in infants born between 22-28 weeks of gestation. Most patients with confirmed NEC develop thrombocytopenia with platelet counts $<100 \times 10^9$/L within 24-48 h of disease onset, and the degree and duration of thrombocytopenia correlates with the severity of bowel injury and adverse clinical outcome. The mechanisms underlying NEC-related thrombocytopenia remain unclear, and these knowledge gaps are an important barrier in determining clinical management and transfusion practices in these critically-ill patients. What is needed are compositions and methods for treating, preventing, and/or inhibiting necrotizing enterocolitis. The methods and compositions disclosed herein address these and other needs.

SUMMARY

Necrotizing enterocolitis (NEC) is an inflammatory bowel necrosis of premature infants and is a leading cause of mortality in premature infants. There are currently no specific therapeutic treatments available for NEC. Disclosed herein, the inventors show that thrombin-mediated platelet activation is a key event during development of NEC and that application of a nanomedicine-based approach to block thrombin activity is used for the treatment of the disease. Thus, disclosed herein is the first specific treatment for NEC.

In some aspect, disclosed herein is a method of treating necrotizing enterocolitis in a subject, comprising administering to the subject a therapeutically effective amount of an antithrombotic nanoparticle comprising a thrombin inhibitor.

In some embodiments, the antithrombotic nanoparticle comprises a core and an outer layer. In some embodiments, the outer layer comprises a lipid component. In some embodiments, the outer layer comprises the thrombin inhibitor. In some embodiments, both the outer layer and the core comprise the thrombin inhibitor.

In some embodiments, the core comprises perfluorocarbon.

In some embodiments, the antithrombotic nanoparticle has a size ranging from about 50 nm to about 1000 nm. In some embodiments, the anti-thrombin nanoparticle has a size about 250 nm.

In some embodiments, the thrombin inhibitor is bivalirudin. In some embodiments, the thrombin inhibitor is D-phenylalanyl-N-[(1S)-4-[(aminoiminomethyl)amino]-1-(2-chloroacetyl)butyl]-L-prolinamide, trifluoroacetate salt (PPACK).

In some embodiments, antithrombotic nanoparticle of any preceding aspects further comprises an antiplatelet agent.

In some embodiments, the outer layer of the antithrombotic nanoparticle further comprises a polypeptide that targets an intestinal endothelial cell.

In some embodiments, the antithrombotic nanoparticle inhibits platelet activation.

In some embodiments, the administration of the antithrombotic nanoparticle decreases a level of tissue factor (TF).

BRIEF DESCRIPTION OF THE FIGURES

The accompanying figures, which are incorporated in and constitute a part of this specification, illustrate several aspects described below.

FIG. 1a shows platelet activation markers during NEC-like neonatal intestinal injury. FACS histograms show platelet expression of a high-affinity conformation of GPIIb/IIIa (cognate antigen for the antibody clone JON/A), PECAM-1/CD31, and P-selectin (CD62P) during intestinal injury. N=10 mice/group, Kruskal Wallis H test with Dunn's post-test for group comparisons; FIG. 1B shows representative aggregation curves for platelets from control and intestinal injury mice (3 h after TNBS), in response to collagen. Platelet aggregation was stimulated with collagen 2.5 µg/mL and optically monitored in a Lumi-Aggregometer. Arrow indicate the point of agonist addition. Scatterplots (means±SEM) on the right summarize the slopes of the aggregation curves in the two groups; N=5 samples/group; each sample was comprised of blood pooled from 4 pups. Mann-Whitney U test; FIG. 1c shows Dense-body content of platelets at various time-points during intestinal injury. Line diagram shows mepacrine fluorescence (means±SEM) in platelets harvested at serial time-points; N=3 samples/time-point (5 mice, 3 total blood draws/pup); Kruskal Wallis H test. Inset: Representative fluorescence images of mepacrine-stained platelets from control and intestinal injury (6 h) pups; FIG. 1d shows that representative transmission electron micrographs (EM) show dense bodies (arrows) in platelets from control and intestinal injury mice, 3 h after initiation of intestinal injury. Scatterplots (means±SEM) on right summarize the dense-body count per platelet, at 3 h and 6 h during intestinal injury. N=5 mice/group; 4 EM images per animal. Kruskal Wallis H test; FIG. 1e shows plasma PF4/CXCL4 concentrations (means±SEM) measured by ELISA during intestinal injury. N=7 control, 11 intestinal injury mice. Kruskal Wallis H test; FIG. if shows representative transmission EM images of platelets from control and intestinal injury mice, harvested at sacrifice (typically 18-24 h into injury protocol). Arrows show α-granules. Scatterplots on right summarize the α-granule count per platelet (means±SEM). N=5 mice/group; 4 EM images per animal. Mann-Whitney U test. * $P<0.05$,  $P<0.01$, * $P<0.001$ vs. control.

FIG. 2a shows platelet counts in P10 mice treated with rat monoclonal anti-GP1bα (0.05 µg/g body weight, intraperitoneal) vs. isotype control; N=7 control, 21 in anti-GP1bα group. Mann-Whitney U test, * P<0.001; FIG. 2b shows that onset of intestinal injury. Kaplan-Meier curves summarize data from animals in control (N=3), intestinal injury (N=8), platelet depletion (N=5), and platelet depletion followed by intestinal injury (N=6) groups. Mantel-Cox log-rank test, * P<0.001; FIG. 2c shows representative photomicrographs (20×) show H&E-stained ileum and colon from the above-listed experimental groups; FIG. 2d shows severity of intestinal injury (means±SEM) graded on an established 5-point scale in the 4 experimental groups; FIG. 2e shows severity of hemorrhages in the intestine (means±SEM) graded similarly in the 4 groups; FIGS. 2f-2i Plasma concentrations of fatty acid-binding protein 2 (FABP2; FIG. 2J), C-reactive protein (CRP; FIG. 2g), CXC-motif ligand 2 (CXCL2; FIG. 2h), and serum amyloid A (SAA; panel FIG. 2i) in the 4 groups. N=6 mice/group;  P<0.01 and * P<0.001 vs. control, ##P<0.01, ###P<0.001 vs. intestinal injury. Kruskal Wallis H test with Dunn's post-test for group comparisons.

FIG. 3a. Circulating platelet activators during murine neonatal intestinal injury. Scatterplots (means±SEM; top to bottom) show plasma thrombin activity, thromboxane A2 (Txa2), endotoxin, and platelet-activating factor (PAF), measured at 0, 2, 3, and 6 h during intestinal injury. N=6 pups; Friedman's test for repeated measures, * P<0.05,  P<0.01, * P<0.001 vs. control;

FIG. 3b. Plasma from mouse pups with intestinal injury activates platelets via thrombin. Scatter bar diagram (means±SEM) shows CD31 expression on platelets from control pups resuspended (×45 min) in plasma from control pups, plasma from pups with intestinal injury, and plasma from pups with intestinal injury with bivalirudin 200 ng/mL to inhibit thrombin. N=3 mice/group; 2 runs; Kruskal Wallis H test with Dunn's post-test for group comparisons, ** P<0.01 vs. control, #P<0.05 vs. intestinal injury; FIG. 3c Thrombin activates platelets during murine neonatal intestinal injury. YFP+ platelets were transfused into WT C57BL/6 pups with intestinal injury, and blood samples were drawn after 3 h. FACS scatter-density plot shows CD31 expression on endogenous (top left) and YFP+ transfused (top right) platelets. Treatment of YFP+ platelets with bivalirudin prior to transfusion blocked activation-related increase in CD31 expression (lower right). Scatterplots at the bottom (means±SEM) summarize these data. N=4 mice/group; Kruskal Wallis H test with Dunn's post-test for group comparisons, * P<0.05 vs. untreated YFP+ platelets, #P<0.05 vs. endogenous platelets in the bivalirudin-treated YFP+ platelet transfusion group.

FIG. 4a Scatter bar diagrams (mean±SEM) shows measured thrombin activity in plasma from P10 pups (left) and adult mice (right) spiked with increasing amounts of mouse recombinant thrombin (0, 7.5, and 15 ng/ml) in vitro. N=5 mice per group; Friedman's test for repeated measures, P<0.01; FIG. 4b. Scatterplots (mean±SEM) plasma concentrations of antithrombin, α1-antitrypsin, α2-macroglobulin, heparin cofactor-II, and tissue factor pathway inhibitor (TFPI) in P10 pups and adult mice. All measurements were performed by ELISA. N=mice/group; Mann-Whitney U test, *P<0.05, *** P<0.001.

FIG. 5a. Scatterplots (means±SEM) show tissue factor (TF) concentrations in plasma and intestinal tissue at serial time points during neonatal intestinal injury, measured by ELISA. N=6 mice/group; Kruskal Wallis H test with Dunn's post-test for group comparisons, * P<0.05,  P<0.01 vs. control; FIG. 5b. Plasma thrombin activity in mouse pups with intestinal injury vs. mouse pups first treated with PCI-27483, which inhibits the tissue factor-factor VII extrinsic pathway tenase complex. N=4 mice/group; Kruskal Wallis H test with Dunn's post-test for group comparisons, *P<0.001 vs. control, ##P<0.01 vs. control treated with PCI-27483; FIG. 5c. Representative fluorescence photomicrographs show immunoreactivity for TF (green) in F4/80+ (red) resident macrophages in control ileum and colon. In the injured ileum and colon, tissue factor immunoreactivity was detectable in macrophages and epithelial cells (open arrows). FIG. 5d Scatter plots on right summarize the fluorescence intensity for TF in control intestinal epithelial cells (IECs), control macrophages, injury IECs, and injury macrophages (top) and in control colonic epithelial cells (CECs), control macrophages, injury CECs, and injury macrophages. N=5 mice/group; Kruskal-Wallis H test with Dunn's post-test, * P<0.001 vs. control epithelial cells, #P<0.05 vs. injury epithelial cells; FIG. 5e Scatter bar diagrams (means±SEM) summarize TF secretion by neonatal intestinal macrophages into microvesicles, when cultured in media alone or after stimulation with LPS (0.5 µg/mL), S. typhimurium flagellin (50 µg/mL), or heat-killed Listeria monocytogenes ($10^8$/mL)×18 h. Kruskal Wallis H test with Dunn's post-test, * P<0.001 vs. media alone. Right: Representative fluorescence images (right) of intestinal macrophages in the 4 groups shows TF immunoreactivity within localized cytoplasmic compartments; FIG. 5f Representative fluorescence photomicrographs of normal adult ileum and colon show the absence of TF immunoreactivity in F4/80+(red, open arrows) macrophages. N=5 mice.

FIG. 6a. Scatterplots (means±SEM) show plasma thrombin activity in mouse pups with intestinal injury, treated with control vs. bivalirudin-tagged nanoparticles. N=4 mice/group; Mann-Whitney U test, * P<0.05; FIG. 6b. Kaplan-Meier curves summarize survival in 4 groups: control, treated with control nanoparticles; control, treated with bivalirudin-tagged nanoparticles; control nanoparticles and intestinal injury; and bivalirudin-tagged nanoparticles and intestinal injury. N=6 pups/group, Mantel-Cox log-rank test, * P<0.001; FIG. 6c. Platelet counts in the 4 experimental groups at sacrifice; FIG. 6d. Representative photomicrographs (20×) show H&E-stained ileum and colon from the above-listed experimental groups. Scale bar=150 µm; FIG. 6e. Severity of intestinal injury (means±SEM) graded on an established 5-point scale in the 4 groups; FIG. 6f Severity of hemorrhages in the intestine (means±SEM) graded similarly in the 4 groups; FIGS. 6g-6j) Plasma concentrations of fatty acid-binding protein 2 (FABP2, panel g), C-reactive protein (CRP; panel h), CXC-motif ligand 2 (CXCL2; panel i), and serum amyloid A (SAA; panel i) in the 4 groups. N=3 each in control and bivalirudin nanoparticle groups, and 6 each in the control nanoparticles with injury and bivalirudin nanoparticles with injury groups;  P<0.01 and *** P<0.001 vs. control, ###P<0.001 vs. control nanoparticle and intestinal injury group. Kruskal Wallis H test with Dunn's post-test for group comparisons.

DETAILED DESCRIPTION

Figures 1A, 1B, 1C, 1D, 1E, 1F:
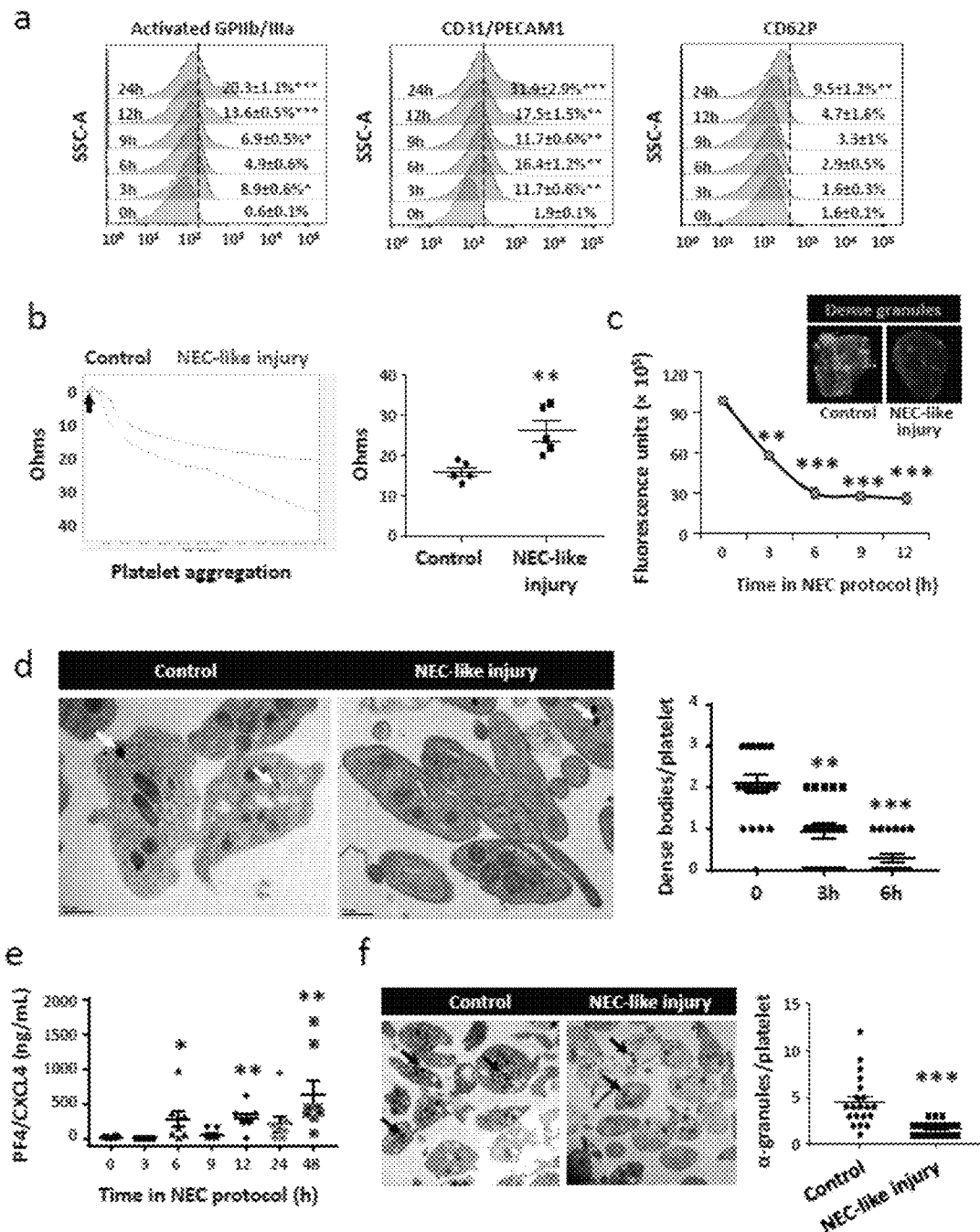
FIGS. 1A-1F. Platelet activation is an early event during murine neonatal intestinal injury.

Necrotizing enterocolitis (NEC) is an idiopathic, inflammatory bowel necrosis of premature infants. Most patients with acute NEC develop thrombocytopenia and often receive one or more platelet transfusions. A neonatal murine model of thrombocytopenia during NEC-like intestinal injury was developed. In this model, NEC-like injury was induced in C57BL/6 mice on postnatal day (P) 10 by enteral administration of the immunogen trinitrobenzene sulfonate (TNBS). TNBS administration in P10 mice induces an acute necrotizing ileocolitis that is distinct from the more subacute colitis induced by TNBS in adult mice, and resembles human NEC in its ileocecal predilection, progression over 24-48 hours, prominence of necrosis and macrophage infiltration, signaling networks, and the dependence on gut microbial flora. In this model, intestinal injury is first detectable on histopathology at about 12 h and thrombocytopenia develops around 15-18 h after TNBS administration. Consistent with clinical observations in human NEC, mice with NEC-like injury show increased immature platelet fractions, larger platelet volumes, and increased megakaryocyte number/ploidy, findings that favored peripheral platelet consumption, not decreased production, as the likely kinetic basis for thrombocytopenia.

The present disclosure shows that platelet activation, as a precursor event to platelet depletion, occurs in murine NEC-like injury once mucosal disruption around 12-15 h, due to bacterial translocation across the damaged mucosa. Platelet activation and granule discharge is a secondary inflammatory event during intestinal injury that augments mucosal damage and the associated systemic inflammation. Platelet activation during NEC-like intestinal injury is an early, thrombin-mediated process that antedated both mucosal damage and the rise in bacterial products in plasma, and is an important pathophysiological event during neonatal intestinal injury.

Therefore, described herein are methods of treating necrotizing enterocolitis in a subject, comprising administering to the subject a therapeutically effective amount of an antithrombotic nanoparticle comprising a thrombin inhibitor.

Reference will now be made in detail to the embodiments of the invention, examples of which are illustrated in the drawings and the examples. This invention may, however, be embodied in many different forms and should not be construed as limited to the embodiments set forth herein.

Unless defined otherwise, all technical and scientific terms used herein have the same meaning as commonly understood to one of ordinary skill in the art to which this disclosure belongs.

Terminology

Terms used throughout this application are to be construed with ordinary and typical meaning to those of ordinary skill in the art. However, Applicant desires that the following terms be given the particular definition as defined below.

As used herein, the article "a," "an," and "the" means "at least one," unless the context in which the article is used clearly indicates otherwise.

The term "comprising" and variations thereof as used herein is used synonymously with the term "including" and variations thereof and are open, non-limiting terms. Although the terms "comprising" and "including" have been used herein to describe various embodiments, the terms "consisting essentially of" and "consisting of" can be used in place of "comprising" and "including" to provide for more specific embodiments and are also disclosed.

As used herein, the terms "may," "optionally," and "may optionally" are used interchangeably and are meant to include cases in which the condition occurs as well as cases in which the condition does not occur. Thus, for example, the statement that a formulation "may include an excipient" is meant to include cases in which the formulation includes an excipient as well as cases in which the formulation does not include an excipient.

The terms "about" and "approximately" are defined as being "close to" as understood by one of ordinary skill in the art. In one non-limiting embodiment, the terms are defined to be within 10%. In another non-limiting embodiment, the terms are defined to be within 5%. In still another non-limiting embodiment, the terms are defined to be within 1%.

"Administration" to a subject includes any route of introducing or delivering to a subject an agent (e.g. an antithrombotic nanoparticle). Administration can be carried out by any suitable route, including oral, topical, intravenous, subcutaneous, transcutaneous, transdermal, intramuscular, intrajoint, parenteral, intra-arteriole, intradermal, intraventricular, intracranial, intraperitoneal, intralesional, intranasal, rectal, vaginal, by inhalation, via an implanted reservoir, or via a transdermal patch, and the like. Administration includes self-administration and the administration by another.

As used herein, the term "subject" can refer to living organisms such as mammals, including, but not limited to humans, livestock, dogs, cats, and other mammals. Administration of the therapeutic agents can be carried out at dosages and for periods of time effective for treatment of a subject. In some embodiments, the subject is a child. In some embodiments, the subject is an infant. In some embodiments, the subject is a premature infant.

A "composition" is intended to include a combination of active agent and another compound or composition, inert (for example, a detectable agent or label) or active, such as a pharmaceutically acceptable carrier or an adjuvant.

The term "nanoparticle" as used herein refers to a particle or structure which is biocompatible with and sufficiently resistant to chemical and/or physical destruction by the environment of such use so that a sufficient number of the nanoparticles remain substantially intact after delivery to the site of application or treatment and whose size is in the nanometer range. For the purposes of the present disclosure, a nanoparticle typically ranges between from about 1 nm to about 1000 nm, or from between about 50 nm and about 500 nm, or from between about 50 nm and about 350 nm, or from between about 100 nm and about 350 nm, between about 120 nm and about 320 nm, between about 140 nm and about 300 nm, between 150 nm and about 280 nm, between 160 nm and about 250 nm, or about 150 nm, about 160 nm, about 170 nm, about 180 nm, about 190 nm, about 200 nm, about 210 nm, about 220 nm, about 230 nm, about 240 nm, or about 250 nm.

"Pharmaceutically acceptable" component can refer to a component that is not biologically or otherwise undesirable, i.e., the component may be incorporated into a pharmaceutical formulation of the disclosure and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents.

As used herein, the term "carrier" encompasses any excipient, diluent, filler, salt, buffer, stabilizer, solubilizer, lipid, stabilizer, or other material well known in the art for use in pharmaceutical formulations. The choice of a carrier for use in a composition will depend upon the intended route of administration for the composition. The preparation of pharmaceutically acceptable carriers and formulations containing these materials is described in, e.g., Remington's Pharmaceutical Sciences, 21st Edition, ed. University of the Sciences in Philadelphia, Lippincott, Williams & Wilkins, Philadelphia, Pa., 2005. Examples of physiologically acceptable carriers include saline, glycerol, DMSO, buffers such as phosphate buffers, citrate buffer, and buffers with other organic acids; antioxidants including ascorbic acid; low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™ (ICI, Inc.; Bridgewater, N.J.), polyethylene glycol (PEG), and PLURONICS™ (BASF; Florham Park, N.J.). To provide for the administration of such dosages for the desired therapeutic treatment, compositions disclosed herein can advantageously comprise between about 0.1% and 99% by weight of the total of one or more of the subject compounds based on the weight of the total composition including carrier or diluent.

"Therapeutically effective amount" or "therapeutically effective dose" of a composition or an agent (e.g. an anti-thrombotic nanoparticle) refers to an amount that is effective to achieve a desired therapeutic result. In some embodiments, a desired therapeutic result is the treatment of necrotizing enterocolitis. In some embodiments, a desired therapeutic result is the treatment of intestinal damage associated with necrotizing enterocolitis. Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as coughing relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

As used herein, the terms "treating" or "treatment" of a subject includes the administration of a drug to a subject with the purpose of curing, healing, alleviating, relieving, altering, remedying, ameliorating, improving, stabilizing or affecting a disease or disorder, or a symptom of a disease or disorder (e.g., necrotizing enterocolitis). The terms "treating" and "treatment" can also refer to reduction in severity and/or frequency of symptoms, elimination of symptoms and/or underlying cause, and improvement or remediation of damage.

The terms "peptide," "protein," and "polypeptide" are used interchangeably to refer to a natural or synthetic molecule comprising two or more amino acids linked by the carboxyl group of one amino acid to the alpha amino group of another.

"Increase" can refer to any change that results in a higher level of gene expression, protein expression, amount of a symptom, disease (e.g., necrotizing enterocolitis), composition, condition (e.g., intestinal damage), or activity. A substance is also understood to increase the level of the gene, the protein, the composition (e.g. tissue factor), or the amount of the condition when the level of the gene, the protein, the composition (e.g. tissue factor), or the amount of the condition is more/higher relative to the output of the level of the gene, the protein, the composition (e.g. tissue factor), or the amount of the condition without the substance. Also, for example, an increase can be a change in the symptoms of a disorder such that the symptoms are less than previously observed. An increase can be any individual, median, or average increase in a condition, symptom, activity, composition in a statistically significant amount. Thus, the increase can be a 1, 2, 3, 4, 5, 6, 7, 8, 9, 10, 15, 20, 25, 30, 35, 40, 45, 50, 55, 60, 65, 70, 75, 80, 85, 90, 95, or 100% increase so long as the increase is statistically significant.

"Decrease" can refer to any change that results in a lower level of gene expression, protein expression, amount of a symptom, disease (e.g., necrotizing enterocolitis), composition, condition (e.g., intestinal damage), or activity. A substance is also understood to decrease the level of the gene, the protein, the composition (e.g. tissue factor), or the amount of the condition when the level of the gene, the protein, the composition (e.g. tissue factor), or the amount of the condition is less/lower relative to the output of the level of the gene, the protein, the composition (e.g. tissue factor), or the amount of the condition without the substance. A decrease can be any individual, median, or average decrease in a condition, symptom, activity, composition in a statistically significant amount. Thus, the decrease can be a 1, 2, 3, 4, 5, 6, 7, 8, 9, 10, 15, 20, 25, 30, 35, 40, 45, 50, 55, 60, 65, 70, 75, 80, 85, 90, 95, or 100% decrease so long as the decrease is statistically significant.

As used herein, "induce", as well as the correlated term "induction", refer to the action of generating, promoting, forming, regulating, activating, enhancing or accelerating a biological phenomenon.

"Inhibit", "inhibiting," and "inhibition" mean to decrease an activity, response, condition, disease, or other biological parameter. This can include but is not limited to the complete ablation of the activity, response, condition, or disease. This may also include, for example, a 10% reduction in the activity, response, condition, or disease as compared to the native or control level. Thus, the reduction can be a 10, 20, 30, 40, 50, 60, 70, 80, 90, 100%, or any amount of reduction in between as compared to native or control levels.

"Activate", "activating", and "activation" mean to increase an activity, response, condition, or other biological parameter. This may also include, for example, a 10% increase in the activity, response, or condition, as compared to the native or control level. Thus, the increase can be a 10, 20, 30, 40, 50, 60, 70, 80, 90, 100%, or any amount of reduction in between as compared to native or control levels.

"Inhibitors," "activators," and "modulators" of expression or of activity are used to refer to inhibitory, activating, or modulating molecules, respectively, identified using in vitro and in vivo assays for expression or activity of a described target protein, e.g., ligands, agonists, antagonists, and their homologs and mimetics. The term "modulator" includes inhibitors and activators. Inhibitors are agents that, e.g., inhibit expression or bind to, partially or totally block stimulation or protease activity (e.g., the protease activity of thrombin), decrease, prevent, delay activation, inactivate, desensitize, or down regulate the activity of the described target protein, e.g., antagonists. Activators are agents that, e.g., induce or activate the expression of a described target protein or bind to, stimulate, increase, open, activate, facilitate, enhance activation or protease inhibitor activity, sensitize or up regulate the activity of described target protein (or encoding polynucleotide), e.g., agonists. Modulators include naturally occurring and synthetic ligands, antagonists and agonists (e.g., small chemical molecules, antibodies and the like that function as either agonists or antagonists). Such assays for inhibitors and activators include, e.g., applying putative modulator compounds to cells expressing the described target protein and then determining the functional effects on the described target protein activity, as described above. Samples or assays comprising described target protein that are treated with a potential activator, inhibitor, or modulator are compared to control samples without the inhibitor, activator, or modulator to examine the extent of effect. Control samples (untreated with modulators) are assigned a relative activity value of 100% Inhibition of a described target protein is achieved when the activity value relative to the control is about 80%, optionally 50% or 25, 10%, 5% or 1%. Activation of the described target protein is achieved when the activity value relative to the control is 110%, optionally 150%, optionally 200, 300%, 400%, 500%, or 1000-3000% or more. In some embodiments, the inhibitor is a thrombin inhibitor. In some embodiments, the thrombin inhibitor is bivalirudin. In some embodiments, the thrombin inhibitor is PPACK.

Antithrombotic Nanoparticles

In some aspects, the present disclosure encompasses an antithrombotic nanoparticle comprising a thrombin inhibitor. Such formulation for the thrombin inhibitor confers a controlled-released and targeted delivery of the thrombin inhibitor in a subject.

As used herein, the term "controlled-release" or "controlled-release drug delivery" refers to release or administration of a drug from a given dosage form in a controlled fashion in order to achieve the desired pharmacokinetic profile in vivo. An aspect of "controlled" drug delivery is the ability to manipulate the formulation and/or dosage form in order to establish the desired kinetics of drug release.

In one aspect of the present disclosure, an effective amount of an active compound as described herein (e.g., a thrombin inhibitor) is incorporated into nanoparticles, e.g. for convenience of delivery and/or extended release delivery. The use of materials in nanoscale provides one the ability to modify fundamental physical properties such as solubility, diffusivity, blood circulation half-life, drug release characteristics, and immunogenicity. In the last two decades, a number of nanoparticle-based therapeutic and diagnostic agents have been developed. These nanoscale agents can provide more effective and/or more convenient routes of administration, lower therapeutic toxicity, extend the product life cycle, and ultimately reduce health-care costs. As therapeutic delivery systems, nanoparticles allow targeted delivery and controlled release.

In addition, nanoparticle-based drug delivery can be used to release drugs at a sustained rate and thus lower the frequency of administration, deliver drugs in a targeted manner to minimize systemic side effects, or deliver two or more drugs simultaneously for combination therapy to generate a synergistic effect and/or suppress drug resistance. To date, a number of nanotechnology-based therapeutic products have been approved for clinical use. Among these products, liposomal drugs and polymer-based conjugates account for more than 80% of the products. See, Zhang, L., et al., Nanoparticles in Medicine: Therapeutic Applications and Developments, *Clin. Pharm. and Ther* 83(5):761-769, 2008.

Nanoparticles may be prepared using a wide variety of methods known in the art. For example, nanoparticles can be formed by methods as nanoprecipitation, flow focusing fluidic channels, spray drying, single and double emulsion solvent evaporation, solvent extraction, phase separation, milling, microemulsion procedures, microfabrication, nanofabrication, sacrificial layers, simple and complex coacervation, and other methods well known to those of ordinary skill in the art. Alternatively or additionally, aqueous and organic solvent syntheses for monodisperse semiconductor, conductive, magnetic, organic, and other nanomaterials have been described (Pellegrino et al., 2005, Small, 1:48; Murray et al., 2000, Ann. Rev. Mat. Sci; 30:545; and Trindade et al., 2001, Chem. Mat., 13:3843). Additional methods have been described in the literature (see, e.g., Doubrow, Ed., "Microcapsules and Nanoparticles in Medicine and Pharmacy," CRC Press, Boca Raton, 1992; Mathiowitz et al., 1987, J. Control. Release, 5:13; Mathiowitz et al., 1987, Reactive Polymers, 6:275; and Mathiowitz et al., 1988, J. Appl. Polymer Sci., 35:755; U.S. Pat. Nos. 5,578,325 and 6,007,845; P. Paolicelli et al., "Surface-modified PLGA-based Nanoparticles that can Efficiently Associate and Deliver Virus-like Particles" Nanomedicine. 5(6):843-853 (2010)).

In some embodiments, the compounds described herein (e.g., a thrombin inhibitor) are associated with a nanoparticle or microsphere (such as a polymeric nanoparticle or polymeric microsphere). Nanoparticles and microspheres may comprise natural polymers, including but not limited to chitosan, alginate, dextran, gelatin, and albumin, and synthetic polymers such as, but not limited to, poly(lactide-co-glycolide) (PLGA), (3-hydroxybutyrate-co-3-hydroxyvalerate) (PHBV), poly(sebacic anhydride), poly(e-caprolactone), polystyrene, thermoresponsive (i.e., NIPAAm and CMCTS-g-PDEA) and pH-responsive (i.e., Eudragit LI 00, Eudragit S and AQOAT AS-MG) polymers.

In one embodiment, the biodegradable controlled-release polymer is selected from poly(lactides), poly(glycolides), poly(lactide-co-glycolides), poly(lactic-acid)s, poly(glycolic acid)s, poly(lactic acid-co-glycolic acid)s, poly(hydroxymethyl glycolide-co-lactide), polycaprolactone, polycarbonates, polyesteramides, polyanhydrides, poly(amino acids), polyorthoesters, polycyanoacrylates, poly(p-dioxanone), poly(alkylene oxalate)s, biodegradable polyurethanes, homopolymers, copolymers, and blended polymers. In one embodiment, the biodegradable controlled-release polymer comprises poly(lactic-co-glycolic acid) (PLGA). PLGA polymers have been used extensively in microspheres, millicylindrical rods, coatings and various other devices, and their rates of degradation and biocompatibility are well understood.

In one embodiment, the polymeric particle, is between about 0.1 nm to about 10000 nm, between about 1 nm to about 1000 nm, between about 10 nm and 1000 nm, between about 100 nm and 800 nm, between about 400 nm and 600 nm, or about 500 nm, between about 100 nm to about 400 nm, between about 100 nm to 300 nm. In one embodiment, the antithrombotic nanoparticle has a size about 0.1 nm, 0.5 nm, 1.0 nm, 5.0 nm, 10 nm, 25 nm, 50 nm, 75 nm, 100 nm, 150 nm, 200 nm, 250 nm, 300 nm, 400 nm, 450 nm, 500 nm, 550 nm, 600 nm, 650 nm, 700 nm, 750 nm, 800 nm, 850 nm, 900 nm, 950 nm, 1000 nm, 1250 nm, 1500 nm, 1750 nm, or 2000 nm.

In one embodiment, the polymeric particle is a antithrombotic nanoparticle, which as a size ranging from 1 nm to 1000 nm, or from between about 50 nm and about 500 nm, or from between about 50 nm and about 350 nm, or from between about 100 nm and about 350 nm, about 100 nm, 110 nm, 120 nm, 130 nm, 140 nm, 150 nm, 160 nm, 170 nm, 180 nm, 190 nm, 200 nm, 210 nm, 220 nm, 230 nm, 240 nm, 250 nm, 260 nm, 270 nm, 280 nm, 290 nm, or 300 nm.

In one embodiment, the compounds (e.g., a thrombin inhibitor) described herein are covalently coupled to a polystyrene particle, PLGA particle, PLA particle, or other microsphere or nanoparticle.

In one aspect, disclosed herein is a controlled-release implant that maintains therapeutic drug levels over time for treatment of necrotizing enterocolitis that is comprised of: a biodegradable controlled-release polymer and a thrombin inhibitor.

In one aspect, the controlled-release pharmaceutical dosage form comprises a biodegradable controlled-release polymer, and a thrombin inhibitor. For example, slow release injectable dosage forms can be used for the management of necrotizing enterocolitis.

An important consideration is the pharmacologic advantage that is provided by controlled release local delivery vehicles. Such a delivery approach avoids peaks and valleys common with other dosage forms such as pills or topical gels. In addition, controlled release local delivery formulations can provide effective drug levels at the treatment site without inducing toxicity away from the treatment sites. This strategy helps eliminate deleterious systemic effects associated with pill or intravenous doing forms.

One aspect of the present disclosure encompasses an antithrombotic nanoparticle. Thrombin is an endolytic serine protease that selectively cleaves fibrinogen to form fibrin and release fibrinopeptide and trigger subsequent fibrin-based blood clotting process. Thrombin also promotes platelet activation and aggregation via activating protease-activated receptors, a subfamily of related G protein-coupled receptors that are activated by cleavage of a part of their extracellular domain. The predominant form of thrombin in vivo is its zymogen, prothrombin (or factor II) is cleaved by the activated protease factor Xa to generate thrombin in the clotting process. As described above, "prothrombin" refers herein to a polypeptide that synthesizes and hydrolyzes cyclic adenosine 5'-diphosphate-ribose, and in humans, is encoded by the F2 gene. In some embodiments, the prothrombin polypeptide is that identified in one or more publicly available databases as follows: HGNC: 3535, Entrez Gene: 2147, Ensembl: ENSG00000180210, OMIM: 176930, UniProtKB: P00734. In some embodiments, the prothrombin polypeptide comprises the wild type sequence of a prothrombin, or a polypeptide sequence having at or greater than about 80%, about 85%, about 90%, about 95%, or about 98% homology with the wild type sequence of a prothrombin, or a polypeptide comprising a portion of the wild type sequence of a prothrombin. The prothrombin polypeptide of the wild type sequence of a prothrombin may represent an immature or pre-processed form of mature prothrombin.

Accordingly, the term "thrombin inhibitor" refers to agents that, e.g., inhibit expression or bind to, partially or totally block stimulation of thrombin or protease activity of thrombin, decrease, prevent, delay activation, inactivate, desensitize, or down regulate the activity of thrombin. In some embodiments, the thrombin inhibitor is selected for the group consisting of bivalirudin and D-phenylalanyl-N-[(1S)-4-[(aminoiminomethyl)amino]-1-(2-chloroacetyl)butyl]-L-prolinamide, trifluoroacetate salt (PPACK).

In some embodiments, the thrombin inhibitor is bivalirudin. Bivalirudin is a synthetic peptide of 20 amino acids, comprising D-Phe, Pro, Arg, Pro, Gly, Gly, Gly, Gly, Asn, Gly, Asp, Phe, Glu, Glu, Ile, Pro, Glu, Glu, Tyr, and Leu in sequence (SEQ ID NO: 1). In some embodiments, the thrombin inhibitor can be a polypeptide comprising SEQ ID NO: 1. In some embodiments, the thrombin inhibitor is PPACK.

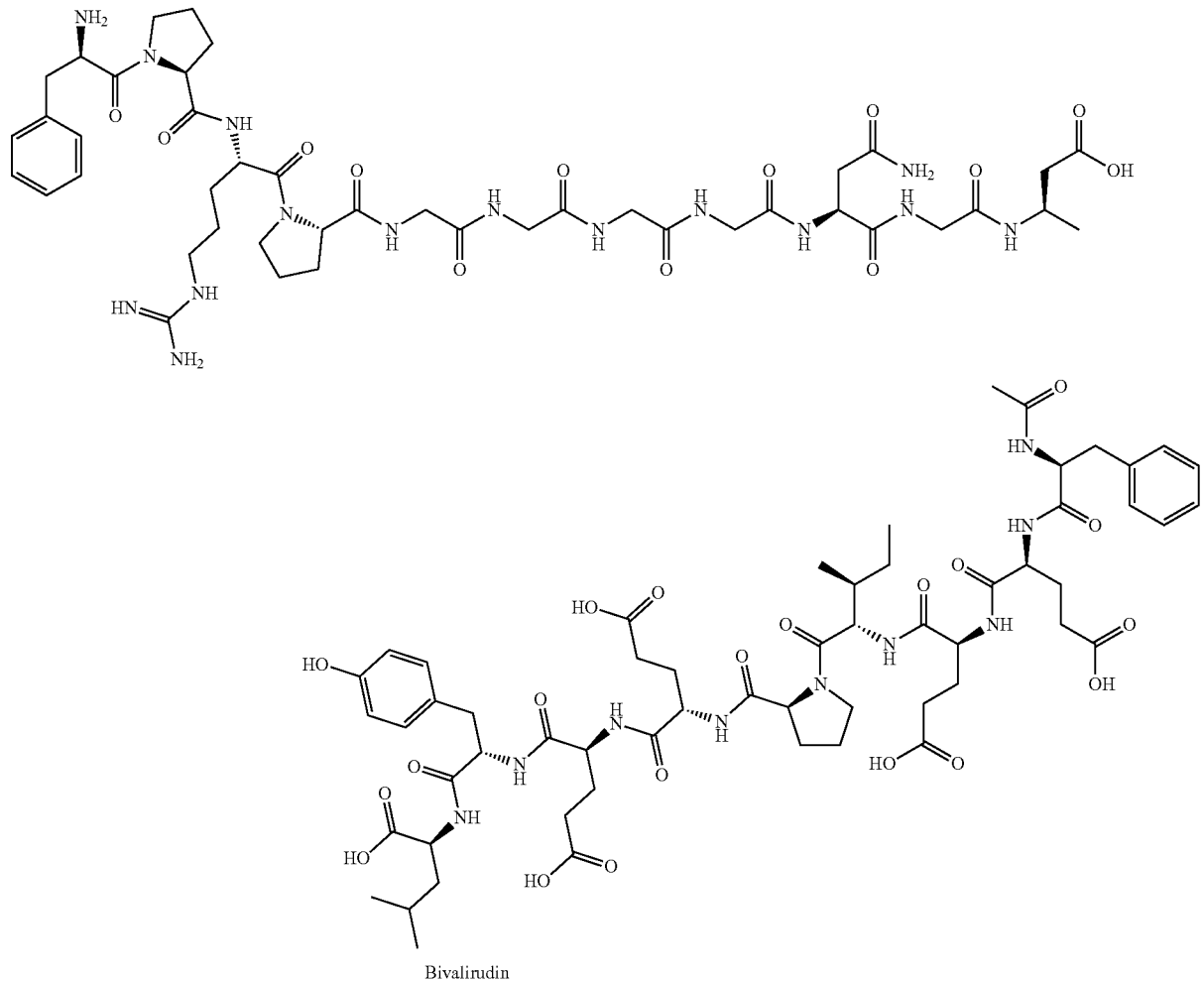

Bivalirudin

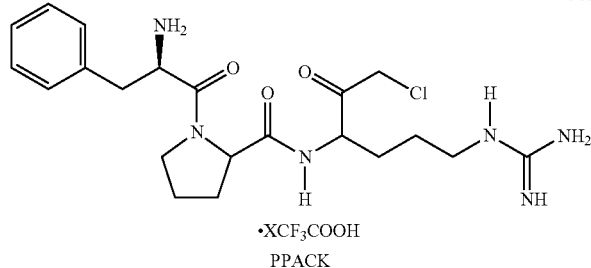

·XCF₃COOH

PPACK

Accordingly, in some embodiments, disclosed herein is a method of threating necrotizing enterocolitis, comprising administering to a subject a therapeutically effective amount of an antithrombotic nanoparticle as disclosed herein, wherein the antithrombotic nanoparticle comprises a thrombin inhibitor, such as bivalirudin and/or PPACK. In one embodiment, an antithrombotic nanoparticle may have anticoagulant activity. In another embodiment, an antithrombotic nanoparticle may have antiplatelet activity. In some embodiments, an antithrombotic nanoparticle may have both anticoagulant activity and antiplatelet activity. "Anti-coagulation activity," as used herein, refers to the ability to decrease fibrin based coagulation. In one embodiment, "antiplatelet activity," as used herein, refers to the ability to decrease platelet activation. In another embodiment, "antiplatelet activity" refers to the ability to decrease the density of platelets in a thrombus. In still another embodiment, "antiplatelet activity" refers to both decreasing the activation of platelets and decreasing the density of platelets in a thrombus. Methods of measuring anticoagulant and antiplatelet activity are known in the art.

In some embodiments, the antithrombotic nanoparticle used herein for treating necrotizing enterocolitis can comprise any thrombin inhibitor (e.g., bivalirudin, hirudin, lepirudin, argatroban, dabigatran, or ximelagatran) and/or any coagulation inhibitors known in the art, such as a vatimin K antagonist (e.g., warfarin, brodifacoum, or difenacoum), heparin or a derivative thereof, a synthetic pentasaccharide inhibitors of factor Xa (e.g., Fondaparinux, idraparinux, or idrabiotaparinux), a directly acting oral anticoagulant (e.g., dabigatran, rivaroxaban, apixaban, edoxaban, or betrixaban), a direct factor Xa inhibitor (e.g., rivaroxaban, apixaban, edoxaban, betrixaban, darexaban, letaxaban, or eribaxaban), batroxobin, or hementin.

The antithrombotic nanoparticle used herein can further comprises an antiplatelet agent, such as an irreversible cyclooxygenase inhibitor (e.g., aspirin or Triflusal (Disgren)), an adenosine diphosphate (ADP) receptor inhibitor (e.g., Cangrelor (Kengreal), Clopidogrel (Plavix), Prasugrel (Effient), Ticagrelor (Brilinta), Ticlopidine (Ticlid)), a phosphodiesterase inhibitor (e.g., Cilostazol (Pletal)), a protease-activated receptor-1 (PAR-1) antagonist (e.g, Vorapaxar (Zontivity)), a glycoprotein IIB/IIIA inhibitor (e.g., Abciximab (ReoPro), Eptifibatide (Integrilin), Tirofiban (Aggrastat)), an adenosine reuptake inhibitor (e.g., Dipyridamole (Persantine)), a thromboxane inhibitors, a thromboxane synthase inhibitor, or a thromboxane receptor antagonist (e.g., Terutroban).

In some embodiments, a nanoparticle of the disclosure, while being antithrombotic at sites of active thrombus formation in a subject, does not substantially alter the clotting time of the subject's plasma. In this regard, "substantially" means that within about 20 min after intravenous administration of the nanoparticle to a subject, the subject's clotting time, as measured by an antithrombotic assay, such as an APTT assay, is about the same as the clotting time in a non-treated plasma sample.

In some embodiments, the antithrombotic nanoparticle disclosed herein comprises a thrombin inhibitor, and wherein the antithrombotic nanoparticle comprises a core and an outer layer. In some embodiments, the outer layer comprises the thrombin inhibitor. In some embodiments, the core comprises the thrombin inhibitor. In some embodiments, both the outer layer and the core comprise the thrombin inhibitor. In some embodiments, the core comprises perfluorocarbon. In some embodiments, antithrombotic nanoparticle comprises a core and an outer layer, wherein the core of the antithrombotic nanoparticle comprises a perfluorocarbon that is a liquid at about 37° C. and the outer layer comprises a mixture of a lipid and a surfactant; wherein the exterior of the antithrombotic nanoparticle comprises a direct thrombin inhibitor covalently conjugated to the exterior via the lipid component of the nanoparticle's outer layer, such that the antithrombotic nanoparticle has a second order kinetic constant for the direct thrombin inhibitor-thrombin interaction that is greater the same kinetic constant of the direct thrombin inhibitor by itself; and wherein the antithrombotic nanoparticle is antithrombotic but does not substantially alter the clotting time of a subject's blood plasma. In some embodiments, the antithrombotic nanoparticle further comprises an antiplatelet agent. Such antithrombotic nanoparticles are known in the art. For instance, see PCT/US2010/061103, US20170065669A1, WO2011084700A1, U.S. Pat. Nos. 5,690,907; 5,780,010; 5,989,520 and 5,958,371, each hereby incorporated by reference in their entirety.

In certain embodiments, the half-life of the antithrombotic nanoparticle after a single intravenous bolus is between about 2 hours and about 4 hours. As used herein, "half-life" refers to the elimination rate of the nanoparticle. In another embodiment, the half-life is between about 2.5 hours and about 3.5 hours. In yet another embodiment, the half-life is between about 2.75 hours and about 3.25 hours. In still another embodiment, the half-life is about 3 hours. In exemplary embodiments, a nanoparticle of the disclosure does not substantially alter the clotting time of the subject's plasma and has a half-life between about 2 hours and about 4 hours after a single intravenous bolus.

It is understood and contemplated herein that a nanoparticle of any preceding aspects may have a more desirable kinetic constant than a thrombin inhibitor by itself.

In certain embodiments, the half-life of the antithrombotic nanoparticle after a single intravenous bolus is about more than 4 hours, 5 hours, 6 hours, 7 hours, 8 hours, 9 hours, 10 hours, 11 hours, 12 hours, 13 hours, 14 hours, 15 hours, 16 hours, 17 hours, 18 hours, 19 hours, 20 hours, 21 hours, 22 hours, 23 hours, 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, 72 hours, or more than 4 days, 5 days, 6 days, 7 days, 8 days, 9 days, 10 days, 11 days, 12 days, 13 days, 14 days, or more than 2 weeks, 3 weeks, or 4 weeks.

It should be noted that the antithrombotic nanoparticle of any preceding aspect for treating necrotizing enterocolitis can be used for targeted delivery. Such nanoparticle can comprise a ligand having specificity for a target.

As used herein, the term "ligand" refers to a biomolecule or a chemical entity having a capacity or affinity for binding to a target. A ligand can include many organic molecules that can be produced by a living organism or synthesized, for example, a protein or portion thereof, a peptide, a polysaccharide, an oligosaccharide, a sugar, a glycoprotein, a lipid, a phospholipid, a polynucleotide or portion thereof, an oligonucleotide, an aptamer, a nucleotide, a nucleoside, DNA, RNA, a DNA/RNA chimera, an antibody or fragment thereof (e.g., Fab, scFv), a receptor or a fragment thereof, a receptor ligand, a nucleic acid-protein fusion, a hapten, a nucleic acid, a virus or a portion thereof, an enzyme, a co-factor, a cytokine, a chemokine, as well as small molecules (e.g., a chemical compound), for example, primary metabolites, secondary metabolites, and other biological or chemical molecules that are capable of activating, inhibiting, or modulating a biochemical pathway or process, and/or any other affinity agent, among others. A ligand can come from many sources, including libraries, such as small molecule libraries, phage display libraries, aptamer libraries, or any other library as would be apparent to one of ordinary skill in the art after review of the disclosure of the present disclosure. In some embodiments, the ligand can be a small molecule or a polypeptide that specifically binds to a receptor on an intestinal endothelial cell.

As used herein, a "target", "target molecule", or "target cell" refers to a biomolecule or a cell that can be the focus of a therapeutic drug strategy, diagnostic assay, or a combination thereof, sometimes referred to as a theranostic. Therefore, a target can include, without limitation, many organic molecules that can be produced by a living organism or synthesized, for example, a protein or portion thereof, a peptide, a polysaccharide, an oligosaccharide, a sugar, a glycoprotein, a lipid, a phospholipid, a polynucleotide or portion thereof, an oligonucleotide, an aptamer, a nucleotide, a nucleoside, DNA, RNA, a DNA/RNA chimera, an antibody or fragment thereof, a receptor or a fragment thereof, a receptor ligand, a nucleic acid-protein fusion, a hapten, a nucleic acid, a virus or a portion thereof, an enzyme, a co-factor, a cytokine, a chemokine, as well as small molecules (e.g., a chemical compound), for example, primary metabolites, secondary metabolites, and other biological or chemical molecules that are capable of activating, inhibiting, or modulating a biochemical pathway or process, and/or any other affinity agent, among others. In some embodiments, the target can be an intestinal endothelial cell. In some embodiments, the target can be a receptor that expressed on an intestinal endothelial cell.

The phrase "having specificity for a target" with respect to the ligand as used herein can also be referred to as the "binding activity" or "binding affinity" of the ligand relative to the target. These phrases may be used interchangeably herein and are meant to refer to the tendency of a ligand to bind or not to bind to a target. The energetics of these interactions are significant in "binding activity" and "binding affinity" because they define the necessary concentrations of interacting ligands and targets, the rates at which these ligands and targets are capable of associating, and the relative concentrations of bound and free ligands and targets. The energetics are characterized through, among other ways, the determination of a dissociation constant, Kd. The specificity of the binding is defined in terms of the comparative dissociation constants (Kd) of the ligand for target as compared to the dissociation constant with respect to the ligand and other materials in the cellular environment or unrelated molecules in general. Typically, the Kd for the ligand with respect to the target will be 2-fold, 5-fold, or 10-fold less than Kd with respect to target and the unrelated material or accompanying material in the cellular environment. The Kd can also be 50-fold less, 100-fold less, or 200-fold less than Kd with respect to target and the unrelated material or accompanying material in the cellular environment.

In an exemplary embodiment of the present disclosure, the target comprises a cellular receptor and the ligand comprises a biomolecule or a chemical compound that has specificity for the receptor. In one embodiment, the target is a cellular receptor that is specifically expressed or overexpressed on a cell of a tissue including, but not limited to, bone, brain, breast, cervix, colon, endometrium, esophagus, eye, gallbladder, head and neck, kidney, liver, lung, lymphoid, mucosal, neuronal, ovary, pancreas, prostate, rectal, skin, stomach, and/or testicles, among others. In some embodiments, the outer layer of the antithrombotic nanoparticle of any preceding aspects comprises a ligand that targets an intestinal endothelial cell. For example, receptors expressed on intestinal endothelial cells, including, for example, ICAM-1 (or CD54), MadCAM-1, and VCAM-1. Accordingly, for delivering the antithrombotic nanoparticle of any preceding aspects to intestine, a ligand comprising a composition that selectively/specifically recognizes a receptor on an intestinal endothelial cell can be incorporated in the antithrombotic nanoparticle.

The ligand can be tethered to the antithrombotic nanoparticle through a linker. Generally, the linker comprises a compound that is capable of one or more of: facilitating covalent, non-covalent, or electrostatic attachment to the surface of the nanoparticle.

In one aspect of the present disclosure, an effective amount of an active compound as described herein (e.g., a thrombin inhibitor) is incorporated microspheres. The microspheres can include, by way of example, glass, ceramic, metal, plastic, or mixtures thereof. In some embodiments, the dosage form comprises a shell and can include a layer of microspheres surrounding the payload and a polymer layer surrounding the layer of microspheres, while in other embodiments, the shell can include multiple payloads (each surrounded by a layer of microspheres) that are agglomerated within a polymer matrix. In any of the above embodiments, the shell can include a layer that is a mixture of microspheres and polymer. See US2015/0164805 (hereby incorporated by reference) for additional discussion of drug delivery using microspheres.

Methods of Treating Necrotizing Enterocolitis (NEC)

Necrotizing enterocolitis (NEC) is an idiopathic, inflammatory bowel necrosis of premature infants. The present disclosure shows platelet activation and depletion develop during neonatal NEC intestinal injury due to the exposure to bacterial products translocated across the damaged mucosal barrier. The neonatal murine model of NEC-like intestinal injury is used herein to study platelet depletion associated with this disease. Platelet activation begins as early as 3 h after 2,4,6-Trinitrobenzenesulfonic acid (TNBS) administration, prior to histopathological evidence of mucosal injury or the rise in plasma LPS levels. This platelet activation is mediated via increased thrombin activity, which is potentiated in neonates by a developmental paucity of endogenous thrombin antagonists such as antithrombotic and α2-macroglobulin. Targeted inhibition of thrombin by intravenous administration of bivalirudin-tagged nanoparticles is protective against both intestinal injury and associated inflammation, without increasing interstitial hemorrhages in the inflamed bowel or other organs.

Therefore, disclosed herein is a method of treating, preventing, inhibiting, and/or reducing necrotizing enterocolitis in a subject, comprising administering to the subject a therapeutically effective amount of an antithrombotic nanoparticle comprising a thrombin inhibitor. In some embodiments, the thrombin inhibitor is selected from the group consisting of bivalirudin and D-phenylalanyl-N-[(1 S)-4-[(aminoiminomethyl)amino]-1-(2-chloroacetyl)butyl]-L-prolinamide and trifluoroacetate salt (PPACK). In some embodiments, the thrombin inhibitor is bivalirudin. In some embodiments, the thrombin inhibitor is PPACK.

D-phenylalanyl-l-prolyl-l-arginyl-chloromethyl ketone (PPACK) is a highly effective irreversible thrombin inhibitor. The molecule has an excellent safety profile in vivo, with an LD50 greater than 50 mg/kg and no long-term toxicity in mice. Nonetheless, therapeutic use of PPACK has been abandoned primarily due to its rapid clearance (7 minute distribution and 2.9 minute elimination half-lives).

Bivalirudin (Hirulog) is a specific and reversible direct thrombin inhibitor (DTI). Bivalirudin inhibits thrombin by specifically binding both to the anion-binding exosite I and to the active site of circulating and clot-bound thrombin. Bivalirudin is a short, synthetic peptide that inhibits both circulating and clot-bound thrombin, while also inhibiting thrombin-mediated platelet activation and aggregation. It does not bind to plasma proteins (other than thrombin) or to red blood cells. Therefore, it has an antithrombotic response. There is no risk for Heparin Induced Thrombocytopenia/Heparin Induced Thrombosis-Thrombocytopenia Syndrome (HIT/HITTS), it does not require a binding cofactor such as antithrombin, and does not activate platelets. Bivalirudin was approved for by FDA for use as an anticoagulant in patients undergoing percutaneous coronary intervention, including patents with HIT/HITTS. However, bivalirudin increases the risk of bleeding in various organs and other side effects. In addition, bivalirudin has a quick onset of action and a short half-life.

Similar side effects of bleeding complication can be found with other anticoagulation medicines. Therefore, a nanoparticle formulation that can prolong the half-life and control the release of an anticoagulation medicine is used for treating necrotizing enterocolitis.

For treating necrotizing enterocolitis, the method disclosed herein comprises using a nanoparticle-based antithrombotic agent that comprises a thrombin inhibitor, such as bivalirudin or PPACK. Such formulation of the thrombin inhibitor prolongs its half-life and reduces drug toxicity. Importantly, the current disclosure shows that intravenous administration of bivalirudin-tagged nanoparticles protects against both intestinal injury and associated inflammation, without increasing interstitial hemorrhages in the inflamed bowel or other organs.

In certain embodiments, the half-life of the antithrombotic nanoparticle after a single intravenous bolus is between about 2 hours and about 4 hours. As used herein, "half-life" refers to the elimination rate of the nanoparticle. In another embodiment, the half-life is between about 2.5 hours and about 3.5 hours. In yet another embodiment, the half-life is between about 2.75 hours and about 3.25 hours. In still another embodiment, the half-life is about 3 hours. In exemplary embodiments, a nanoparticle of the disclosure does not substantially alter the clotting time of the subject's plasma and has a half-life between about 2 hours and about 4 hours after a single intravenous bolus.

It is understood and contemplated herein that a nanoparticle of any preceding aspects may have a more desirable kinetic constant than a thrombin inhibitor by itself.

In certain embodiments, the half-life of the antithrombotic nanoparticle after a single intravenous bolus is between more than 4 hours, 5 hours, 6 hours, 7 hours, 8 hours, 9 hours, hours, 11 hours, 12 hours, 13 hours, 14 hours, 15 hours, 16 hours, 17 hours, 18 hours, 19 hours, 20 hours, 21 hours, 22 hours, 23 hours, 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, 72 hours, or more than 4 days, 5 days, 6 days, 7 days, 8 days, 9 days, 10 days, 11 days, 12 days, 13 days, 14 days, or more than 2 weeks, 3 weeks, or 4 weeks.

In some embodiments, the present disclosure includes a method of treating necrotizing enterocolitis, comprising administering to a subject a therapeutically effective amount of the antithrombotic nanoparticle of any preceding aspects, wherein the nanoparticle comprises a ligand having specificity for a target. As noted above, the term "ligand" refers to a biomolecule or a chemical entity having a capacity or affinity for binding to a target. In some embodiments, the ligand targets an intestinal endothelial cell. In some embodiments, the ligand targets a receptor on an intestinal endothelial cell.

For example, the ligand may be able to efficiently bind to or otherwise associate with a biological entity, for example, a particular membrane component or cell surface receptor. Targeting of an antithrombotic nanoparticle to a particular tissue or cell type, and/or to a specific diseased tissue (e.g., inflamed intestinal tissue or intestinal endothelial cells) but not to normal tissue, is desirable for the treatment of tissue specific diseases such as necrotizing enterocolitis. For example, in contrast to systemic delivery of a toxic thrombin inhibitor, the nanoparticles comprising the tissue-targeting ligand disclosed herein may substantially prevent the thrombin inhibitor from affecting healthy cells. Additionally, disclosed nanoparticles may allow for the administration of a lower dose of the agent (as compared to an effective amount of agent administered without disclosed nanoparticles or nanoparticles with the ligand described above) which may reduce the undesirable side effects commonly associated with traditional anticoagulation therapy.

As noted above, the antithrombotic nanoparticle used herein for treating necrotizing enterocolitis can comprise any thrombin inhibitors (e.g., bivalirudin, hirudin, lepirudin, argatroban, dabigatran, or ximelagatran) and/or any coagulation inhibitor known in the art, such as a vatimin K antagonist (e.g., warfarin, brodifacoum, or difenacoum), heparin or a derivative thereof, a synthetic pentasaccharide inhibitors of factor Xa (e.g., Fondaparinux, idraparinux, or idrabiotaparinux), a directly acting oral anticoagulant (e.g., dabigatran, rivaroxaban, apixaban, edoxaban, or betrixaban), a direct factor Xa inhibitor (e.g., rivaroxaban, apixaban, edoxaban, betrixaban, darexaban, letaxaban, or eribaxaban), batroxobin, or hementin.

Further, as noted above, in some embodiments, the antithrombotic nanoparticle used herein can further comprises an antiplatelet agent, such as such as an irreversible cyclooxygenase inhibitor (e.g., aspirin or Triflusal (Disgren)), an adenosine diphosphate (ADP) receptor inhibitor (e.g., Cangrelor (Kengreal), Clopidogrel (Plavix), Prasugrel (Effient), Ticagrelor (Brilinta), Ticlopidine (Ticlid)), a phosphodiesterase inhibitor (e.g., Cilostazol (Pletal)), a protease-activated receptor-1 (PAR-1) antagonist (e.g, Vorapaxar (Zontivity)), a glycoprotein IIB/IIIA inhibitor (e.g., Abciximab (ReoPro), Eptifibatide (Integrilin), Tirofiban (Aggrastat)), an adenosine reuptake inhibitor (e.g., Dipyridamole (Persantine)), a thromboxane inhibitors, a thromboxane synthase inhibitor, or a thromboxane receptor antagonist (e.g., Terutroban).

Accordingly, in some embodiments, the current disclosure shows a method of treating, preventing, reducing, and/or inhibiting necrotizing enterocolitis in a subject, comprising administering to the subject a therapeutically effective amount of an antithrombotic nanoparticle of any preceding aspects comprising a thrombin inhibitor, wherein the antithrombotic nanoparticle further comprises an antiplatelet agent, and wherein the antithrombotic nanoparticle inhibits platelet activation.

In some embodiments, the method of treating necrotizing enterocolitis comprises administering to the subject a therapeutically effective amount of an antithrombotic nanoparticle of any preceding aspects, wherein the antithrombotic nanoparticle comprises a thrombin inhibitor, and wherein the antithrombotic nanoparticle comprises a core and an outer layer. In some embodiments, the outer layer comprises the thrombin inhibitor. In some embodiments, the core comprises the thrombin inhibitor. In some embodiments, both the outer layer and the core comprise the thrombin inhibitor. In some embodiments, the core comprises perfluorocarbon. In some embodiments, antithrombotic nanoparticle comprises a core and an outer layer, wherein the core of the antithrombotic nanoparticle comprises a perfluorocarbon that is a liquid at about 37° C. and the outer layer comprises a mixture of a lipid and a surfactant; wherein the exterior of the antithrombotic nanoparticle comprises a direct thrombin inhibitor covalently conjugated to the exterior via the lipid component of the nanoparticle's outer layer, such that the antithrombotic nanoparticle has a second order kinetic constant for the direct thrombin inhibitor-thrombin interaction that is greater the same kinetic constant of the direct thrombin inhibitor by itself; and wherein the antithrombotic nanoparticle is antithrombotic but does not substantially alter the dotting time of a subject's blood plasma. In some embodiments, the antithrombotic nanoparticle further comprises an antiplatelet agent. Such antithrombotic nanoparticles are known in the art. For instance, see PCT/US2010/061103, US20170065669A1, WO2011084700A1, U.S. Pat. Nos. 5,690,907; 5,780,010; 5,989,520 and 5,958, 371, each hereby incorporated by reference in their entirety.

Tissue factor (TF) is a 30-kDa transmembrane glycoprotein encoded by gene F3. In some embodiments, the TF polypeptide is that identified in one or more publicly available databases as follows: HGNC: 3541, Entrez Gene: 2152, Ensembl: ENSG00000117525, OMIM: 134390, UniProtKB: P13726. TF is expressed on subendothelial smooth muscle, epithelia, circulating leukocytes, and platelets. TF is known to provide a protective hemostatic envelope; if the vessel wall is injured, subendothelial TF is exposed and becomes available to complex with circulating factor VII, activating coagulation cascades that eventually lead to thrombin generation. In some embodiments, administration of the antithrombotic nanoparticle of any preceding aspects decreases a level of TF.

In some embodiments, the method of any preceding aspects decreases intestinal damage. As noted above, necrotizing enterocolitis is associated with bacteria invasion across the intestinal barrier, causing local infection and inflammation that may destroy the wall of bowel. Accordingly, the term "decreases intestinal damage" can refer to decreases of intestinal inflammation, decreases of bacteria invasion across the intestinal barrier, decreases of local or systematic bacterial load, and/or increases of intestinal barrier integrity.

As the timing of necrotizing enterocolitis can often not be predicted, it should be understood the disclosed methods of treating, preventing, reducing, and/or inhibiting necrotizing enterocolitis comprising administering to a subject a therapeutically effective amount of an antithrombotic nanoparticle, can be used prior to or following the onset of the disease, to treat, prevent, inhibit, and/or reduce the disease. Herein, the disclosed methods can be performed any time prior to onset of the disease. In one aspect, the disclosed methods can be employed 12, 11, 10, 9, 8, 7, 6, 5, 4, 3, 2, 1 months, 30, 29, 28, 27, 26, 25, 24, 23, 22, 21, 20, 19, 18, 17, 16, 15, 14, 13, 12, 11, 10, 9, 8, 7, 6, 5, 4, 3 days, 60, 48, 36, 30, 24, 18, 15, 12, 10, 9, 8, 7, 6, 5, 4, 3, 2 hours, 60, 45, 30, 15, 10, 9, 8, 7, 6, 5, 4, 3, 2, or 1 minute prior to necrotizing enterocolitis, even prior to onset of intestinal inflammation; or 1, 2, 3, 4, 5, 6, 7, 8, 9, 10, 15, 20, 25, 30, 35, 40, 45, 50, 55, 60, 75, 90, 105, 120 minutes, 3, 4, 5, 6, 7, 8, 9, 10, 11, 12, 15, 18, 24, 30, 36, 48, 60 hours, 3, 4, 5, 6, 7, 8, 9, 10, 11, 12, 13, 14, 15, 16, 17, 18, 19, 20, 21, 22, 23, 24, 25, 26, 27, 28, 29, 30, 45, 60, 90 or more days, 4, 5, 6, 7, 8, 9, 10, 11, 12 or more months 5, 4, 3, 2, 1 years after necrotizing enterocolitis.

EXAMPLES

The following examples are set forth below to illustrate the compounds, systems, methods, and results according to the disclosed subject matter. These examples are not intended to be inclusive of all aspects of the subject matter disclosed herein, but rather to illustrate representative methods and results. These examples are not intended to exclude equivalents and variations of the present disclosure which are apparent to one skilled in the art.

Example 1. Platelet Activation is an Early Event During Murine Neonatal Intestinal Injury To investigate platelet activation in a neonatal murine model of NEC-related thrombocytopenia, [Namachivayam K, et al. Neonatal Mice with Necrotizing Enterocolitis-like Injury Develop Thrombocytopenia despite Increased Megakaryopoiesis. *Pediatr Res.* 2017; 81:817-824; MohanKumar K, et al. Gut mucosal injury in neonates is marked by macrophage infiltration in contrast to pleomorphic infiltrates in adult: evidence from an animal model. *Am J Physiol Gastrointest Liver Physiol.* 2012; 303(1):G93-102; MohanKumar K, et al. Trinitrobenzene Sulfonic Acid-induced Intestinal Injury in Neonatal Mice Activates Transcriptional Networks Similar to those seen in Human Necrotizing Enterocolitis. *Pediatr Res.* 2016; 81(1):99-112; MohanKumar K, et al. Smad7 Interrupts TGF-β Signaling in Intestinal Macrophages and Promotes Inflammatory Activation of these Cells during Necrotizing Enterocolitis. *Pediatr Res.* 2016; 79(6):951-961] circulating platelets were evaluated for 3 activation markers: activated GPIIb/IIIa (cognate epitope for the antibody JON/A), [Bergmeier W, et al. Flow cytometric detection of activated mouse integrin alphaIIb-beta3 with a novel monoclonal antibody. *Cytometry.* 2002; 48(2):80-86] CD31/platelet endothelial cell adhesion molecule (PECAM)-1, and P-selectin (CD62P; FIG. 1a). Platelet immunoreactivity for activated GPIIb/IIIa and CD31 rose as early as 3 h after TNBS administration. Neonatal platelets showed low baseline expression of CD62P and upregulated it more slowly than other markers. At the 3 h time-point, there was no change in platelet counts (mean±SE 660±26× $10^9$/L in control vs. 664±13×$10^9$/L in intestinal injury).

Figure 7:
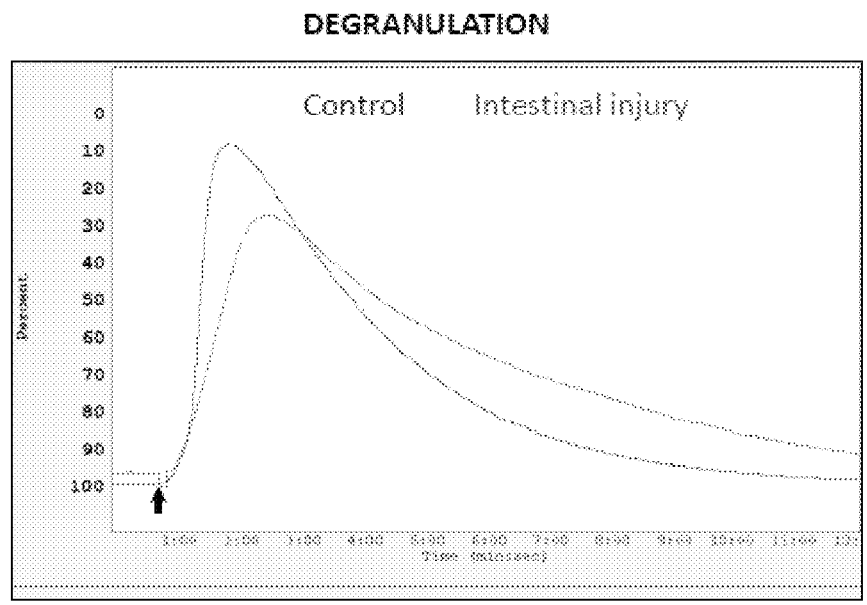
FIG. 7. Representative curves showing ATP release as a marker for dense granule secretion from platelets isolated from control and intestinal injury mice (3 h after TNBS administration), in response to collagen. ATP release was measured using a luciferin/luciferase method (with an ATP standard) in a Lumi-Aggregometer. Arrow indicates the point of agonist addition. Test samples were comprised of blood pooled from 4 pups each. Data are representative of 2 separate experiments.

Intestinal injury was also associated with platelet hyperaggregability at the 3 h time-point (tested with collagen, which was used as a generic tissue injury-related stimulus; FIG. 1b). Platelet dense granule content was evaluated by staining platelets with mepacrine ex vivo; [Wall J E, et al. A flow cytometric assay using mepacrine for study of uptake and release of platelet dense granule contents. *Br J Haematol.* 1995; 89(2):380-385] there was a significant loss of mepacrine fluorescence in circulating platelets beginning at 3 h indicating dense granule discharge (FIG. 1c). Consistent with these data, fewer dense granules per platelet were also detected at the 3 h time-point on electron microscopy (FIG. 1d), and increased collagen-stimulated ATP release in a lumi-aggregometer (FIG. 7).

Although platelet CD31 expression was upregulated early, other α-granule contents may have been released more slowly during intestinal injury. Plasma concentrations of platelet factor (PF)-4/CXC motif ligand (CXCL) 4 began rising at 6 h and continued to increase until 24-48 h (FIG. 1e). Electron micrographs showed depletion of platelet α-granules at 18 h (FIG. 10, but not at earlier time-points.

Taken together, increased platelet surface activation markers, hyperaggregability, and granule discharge as early as 3 h after TNBS administration indicated that platelet activation was an early event during neonatal intestinal injury, showing that platelet activation can begin before any histopathological evidence of intestinal injury. [Namachivayam K, et al. Neonatal Mice with Necrotizing Enterocolitis-like Injury Develop Thrombocytopenia despite Increased Megakaryopoiesis. *Pediatr Res.* 2017; 81:817-824; MohanKumar K, et al. Trinitrobenzene Sulfonic Acid-induced Intestinal Injury in Neonatal Mice Activates Transcriptional Networks Similar to those seen in Human Necrotizing Enterocolitis. *Pediatr Res.* 2016; 81(1):99-112; MohanKumar K, et al. Smad7 Interrupts TGF-β Signaling in Intestinal Macrophages and Promotes Inflammatory Activation of these Cells during Necrotizing Enterocolitis. *Pediatr Res.* 2016; 79(6):951-961.]

In addition, platelet CD31 expression and mepacrine staining of dense granules were used to measure platelet activation because these tests can be performed with 20 µL of blood and thus, allowed for non-terminal, repeated in-vivo measurements in P10 mice. Platelet aggregability and ATP release provided useful data but required ≥250 µL blood that had to be pooled from ≥4 pups per experiment.

Example 2. Platelet Depletion Protects Against Neonatal Intestinal Injury

Figures 2A, 2B, 2C, 2D, 2E, 2F, 2G, 2H, 2I:
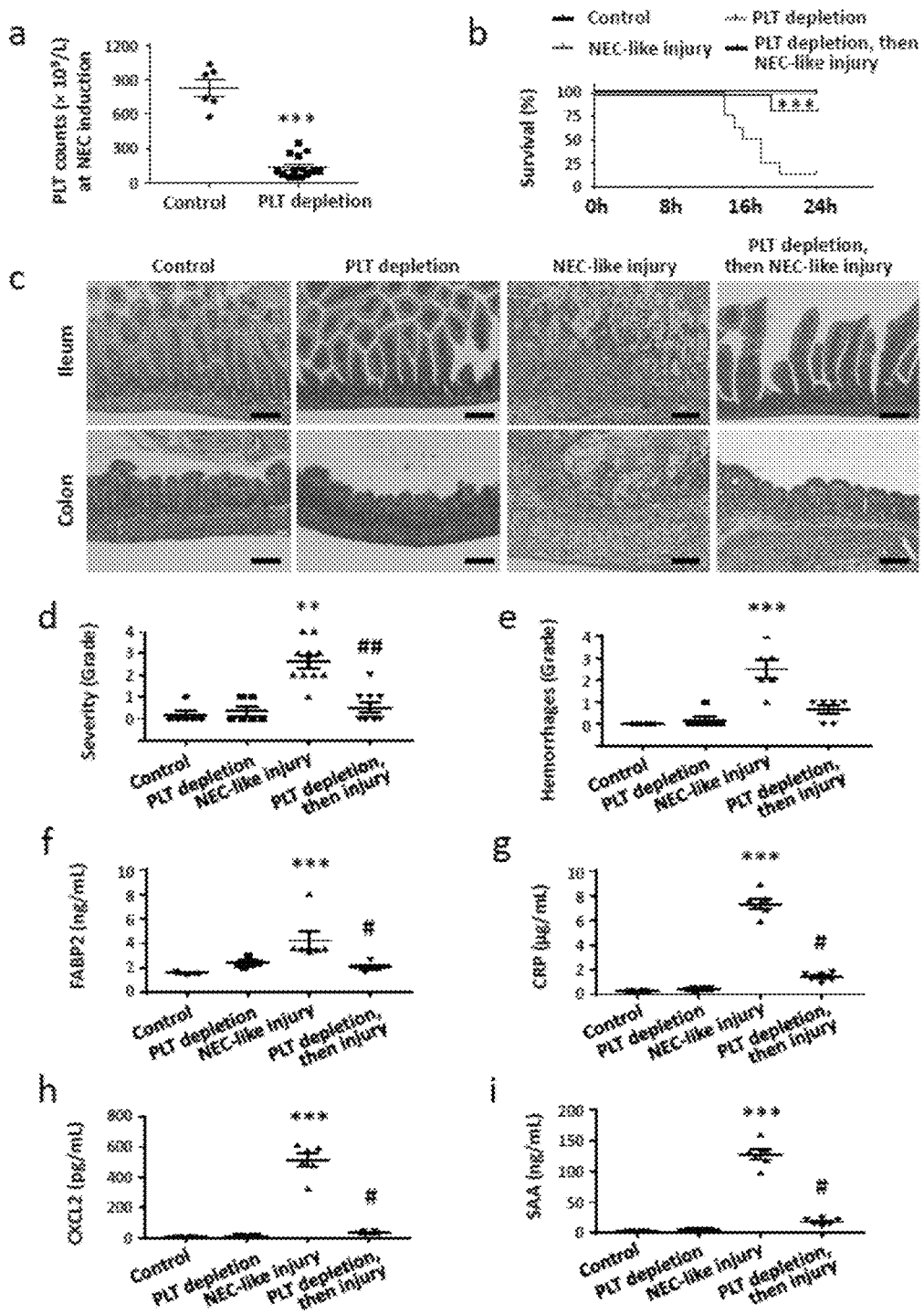
FIGS. 2A-2I. Platelet depletion protects against neonatal intestinal injury.
Figure 8:
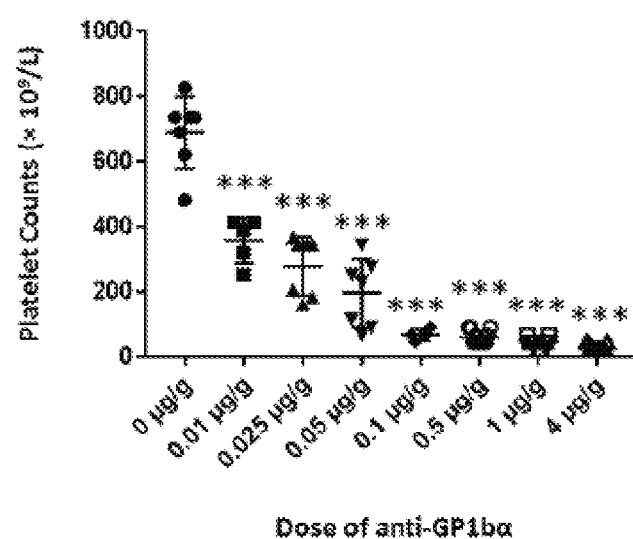
FIG. 8. Antibody-mediated platelet depletion. Intraperitoneal administration of rat monoclonal anti-GP1bα/CD42b reduced platelet counts within 12 h in a dose-dependent fashion. Scatterplots (means±SEM) summarize platelet counts in various antibody dose groups. N=4-10 pups per group; Kruskal Wallis H test with Dunn's post-test for group comparisons; *** $P<0.001$ vs. control.

To determine the pathophysiological relevance of the early platelet activation observed in NEC-like intestinal injury, some animals were subjected first to antibody-mediated platelet depletion and then induced intestinal injury. These pups were treated with rat monoclonal anti-GP1bα (0.05 µg/g body weight, intraperitoneal; FIG. 2a; dose based on studies shown in FIG. 8) to deplete platelet counts to 50-100×$10^9$/L, levels seen during moderate-severe murine NEC-like intestinal injury. [Namachivayam K, et al. Neonatal Mice with Necrotizing Enterocolitis-like Injury Develop Thrombocytopenia despite Increased Megakaryopoiesis. *Pediatr Res.* 2017; 81:817-824] Platelet depletion reduced both mortality and the severity of intestinal injury (FIGS. 2b, 2c and 2d) without increasing the severity of hemorrhages into the injured intestine or in remote organs (FIG. 2e). The protective effect of platelet depletion on bowel injury was further evident in in lower plasma levels of fatty acid binding protein (FABP)-2, a cytosolic protein of enterocytes that is a useful biochemical marker of gut mucosal injury [MohanKumar K, et al. Intestinal epithelial apoptosis initiates gut mucosal injury during extracorporeal membrane oxygenation in the newborn piglet. *Lab Invest.* 2014; 94(2):150-160.] (FIG. 2f). These animals also had less systemic inflammation, as evident from lower plasma levels of C-reactive protein, CXCL2, and serum amyloid A (FIGS. 2g, 2h, and 2i), three inflammatory markers associated with human NEC and murine NEC-like injury. [Ng P C. Biomarkers of necrotising enterocolitis. *Semin Fetal Neonatal Med.* 2014; 19(1):33-38.]

Example 3. Thrombin Activates Platelets During Neonatal Intestinal Injury

Figure 9:
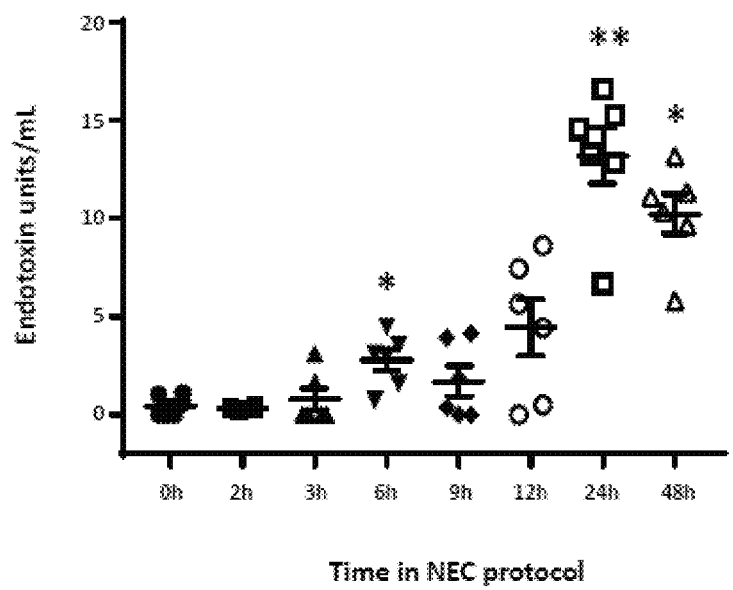
FIG. 9. Scatterplots (means±SEM) summarize plasma endotoxin levels during NEC-like neonatal intestinal injury. Endotoxin levels were measured by the limulus lysate assay N=6 pups/group; Kruskal Wallis H test with Dunn's post-test for group comparisons; * $P<0.05$, ** $P<0.01$ vs. control.
Figure 10:
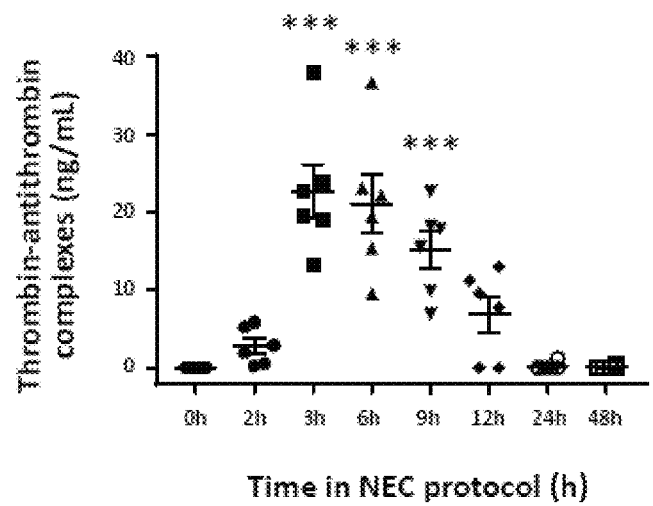
FIG. 10. Scatterplots (means±SEM) summarize plasma concentrations of thrombin-antithrombin complexes during NEC-like neonatal intestinal injury. N=6 pups/group; Kruskal Wallis H test with Dunn's post-test for group comparisons; *** $P<0.001$ vs. control.

To identify the stimuli that activated platelets during neonatal intestinal injury, thrombin activity, thromboxane A2 (txA2), endotoxin, and platelet activating factor (PAF) were measured in plasma samples collected at early time-points (<6 h). Plasma thrombin activity was increased at 3 h. There was no change in txA2, whereas endotoxin and PAF levels began to rise only at 6 h (FIG. 3a; FIG. 9). Further evidence for thrombin generation was seen in elevated plasma concentrations of thrombin-antithrombotic complexes at 3 h and beyond (FIG. 10).

Figures 3A, 3B, 3C:
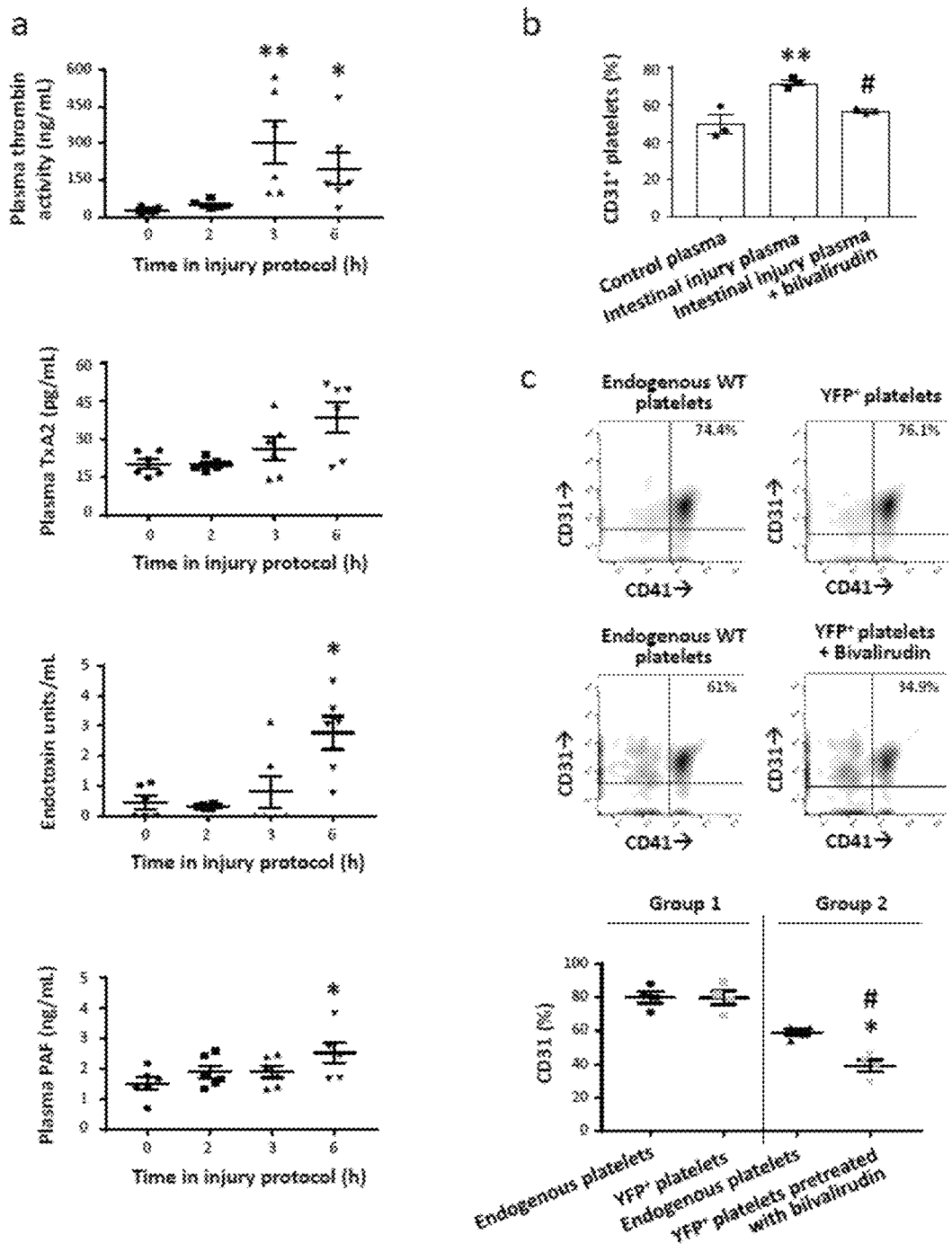
FIGS. 3A-3C. Thrombin activates platelets during neonatal intestinal injury.
Figures 11A, 11B:
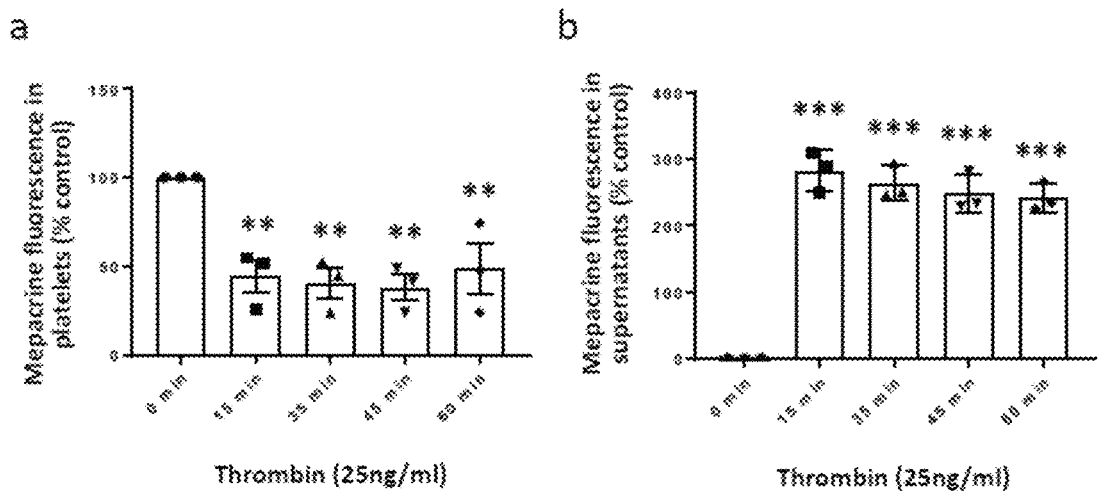
FIGS. 11A and 11B. Scatter bar diagrams (means±SEM) show (A) mepacrine fluorescence signal in platelets isolated from control P10 mice at serial time-points after treatment with recombinant thrombin (25 ng/mL). Fluorescence signal normalized and depicted as percent of control. Data represent 3 separate experiments; each experiment included platelets pooled from 3 pups; (B) mepacrine fluorescence signal released into the supernatant after thrombin stimulation. Kruskal Wallis H test with Dunn's post-test for group comparisons;  $P<0.01$, * $P<0.001$ vs. control.
Figures 12A, 12B:
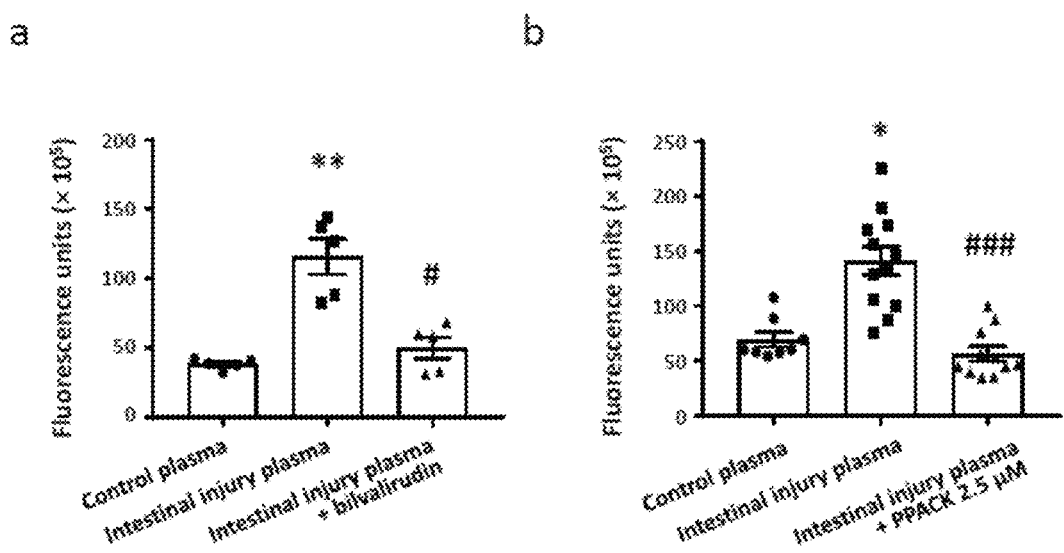
FIGS. 12A and 12B. (A) Scatter bar diagrams (means±SEM) show mepacrine fluorescence signal released from control P10 platelets into the supernatant, following resuspension in plasma from pups in (1) control group; (2) intestinal injury at 3 h; and (3) intestinal injury at 3 h with added bivalirudin, a synthetic peptide inhibitor of thrombin. N=6 mice/group; (B) mepacrine fluorescence released from control platelets following resuspension in plasma from (1) control group (N=8 mice); (2) intestinal injury at 3 h (N=12 mice); and (3) intestinal injury at 3 h with added D-phenylalanyl-prolyl-arginyl chloromethyl ketone (PPACK), a different thrombin inhibitor (N=11 mice). Kruskal Wallis H test with Dunn's post-test for group comparisons; * $P<0.05$, ** $P<0.01$ vs. control; #$P<0.05$, ###$P<0.001$ vs. intestinal injury plasma.

Neonatal platelets can be hyporesponsive under specific conditions, [Mull M M, Hathaway W E. Altered platelet function in newborns. *Pediatr Res.* 1970; 4(3):229-237] and therefore, the ability of neonatal murine platelets to respond to thrombin was checked. Treatment of mepacrine-stained P10 platelets with recombinant thrombin (25 µg/mL) caused dense granule discharge within 15 min (FIG. 11). Next, to determine the contribution of thrombin to platelet activation during NEC-like intestinal injury, a mixing experiment was performed for measuring platelet activation following resuspension in plasma from (1) control pups; (2) intestinal injury at 3 h; and (3) intestinal injury at 3 h with added bivalirudin, a synthetic peptide inhibitor of thrombin. [Gladwell T D. Bivalirudin: a direct thrombin inhibitor. *Clin Ther.* 2002; 24(1):38-58.] Exposure to plasma from mice with intestinal injury caused platelet dense granule discharge, which was blocked by bivalirudin (FIG. 12a). Similar results were observed upon replacement of bivalirudin with D-phenyl-alanyl-prolyl-arginyl chloromethyl ketone (PPACK), [Schmaier A H, et al. PPACK-thrombin is a noncompetitive inhibitor of alpha-thrombin binding to human platelets. *Thromb Res.* 1992; 67(5):479-489] another synthetic peptide inhibitor of thrombin-mediated platelet activation (FIG. 12b). Bivalirudin also blocked the effects of intestinal injury plasma on platelet CD31 expression (FIG. 3b). These findings indicated an important role of thrombin in activating platelets during NEC-like injury.

Figure 13:
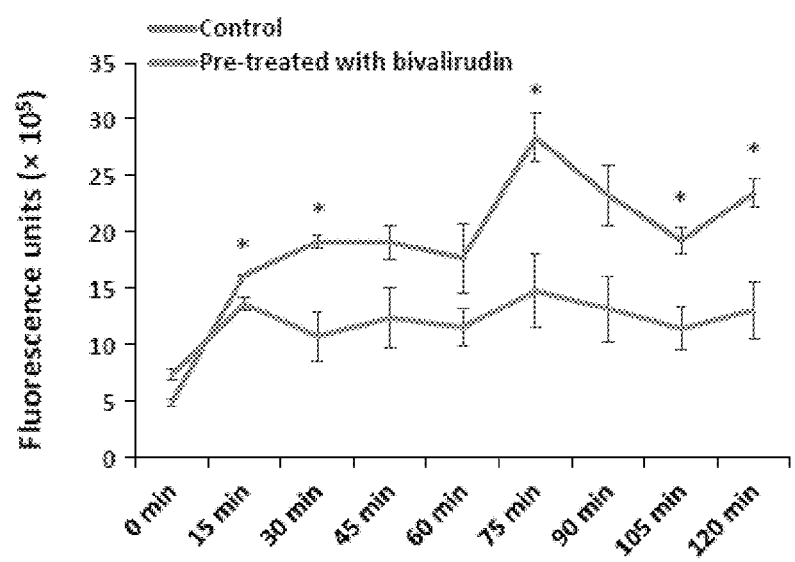
FIG. 13. Line diagrams (means±SEM) show mepacrine fluorescence signal released over time from control (blue) and bivalirudin-treated and washed (orange) P10 platelets into the supernatant, following treatment with thrombin (25 ng/mL). Data represent 3 separate experiments; each experiment included platelets pooled from 3 pups; Kruskal Wallis H test with Dunn's post-test for group comparisons; * $P<0.05$ vs. control.

In vivo assessment was performed for thrombin-mediated platelet activation during neonatal intestinal injury. First, to determine the duration of bivalirudin inhibition of thrombin-mediated platelet activation after a point-exposure, P10 platelets were treated with mepacrine and bivalirudin in vitro and washed before the addition of recombinant thrombin. Control platelets showed thrombin-mediated dense granule discharge within 15 min, whereas bivalirudin-treated platelets remained refractory to thrombin over 120 min (FIG. 13). In the next in vivo study, wild-type neonatal mice 3 h into intestinal injury were transfused with platelets expressing enhanced yellow fluorescence protein (YFP; platelets harvested from progeny of PF4-cre mice (C57BL/6-Tg(Cxcl4-cre)Q3Rsko/J)×R26-stop-YFP mutant mice (B6.129X1-Gt(ROSA)26Sortm1(EYFP)Cos/J). In some mice, YFP+ platelets were pre-treated with bivalirudin prior to transfusion, and CD31 expression was then measured for both the endogenous and the bivalirudin-treated transfused YFP+ platelets in blood samples drawn 3 h after the transfusion. Bivalirudin-pretreatment curtailed CD31 expression on YFP+ platelets (FIG. 3c), providing further evidence for a role of thrombin as the primary platelet activator in NEC-like neonatal intestinal injury.

Figure 14A:
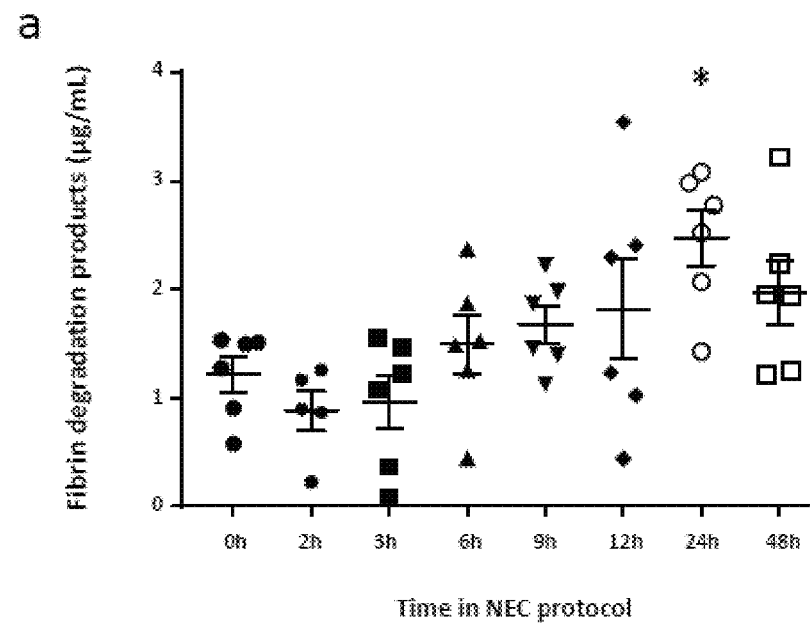
FIGS. 14A and 14B. (A) Scatterplots (means±SEM) summarize plasma concentrations of fibrin degradation products (FDP; μg/mL) during NEC-like neonatal intestinal injury. N=6 pups/group; Kruskal Wallis H test with Dunn's post-test for group comparisons; * $P<0.05$ vs. control; (B) Scatterplot depicts plasma FDP concentrations and platelet counts. N=33 mice. Spearman's correlation: r=−0.168; p=0.3; linear regression: $r^2=0.077$.
Figure 14B:
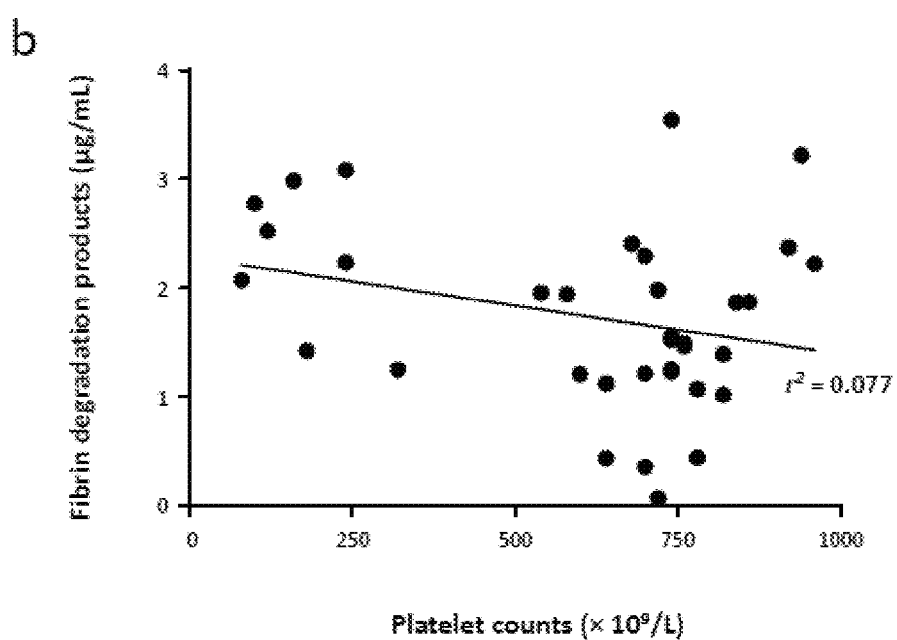

These data show that platelet activation, thrombocytopenia, and thrombin generation were not likely to be related to disseminated intravascular coagulation (DIC). There was no change in plasma concentrations of fibrin degradation products (FDPs) until 24 h (FIG. 14a). Furthermore, FDP concentrations did not predict thrombocytopenia; in regression analysis, FDP concentrations accounted for only 7.7% of the variability in platelet counts (FIG. 14b).

Example 4. Regulators of Thrombin Activity in Pups and Adult Plasma

Figures 4A, 4B:
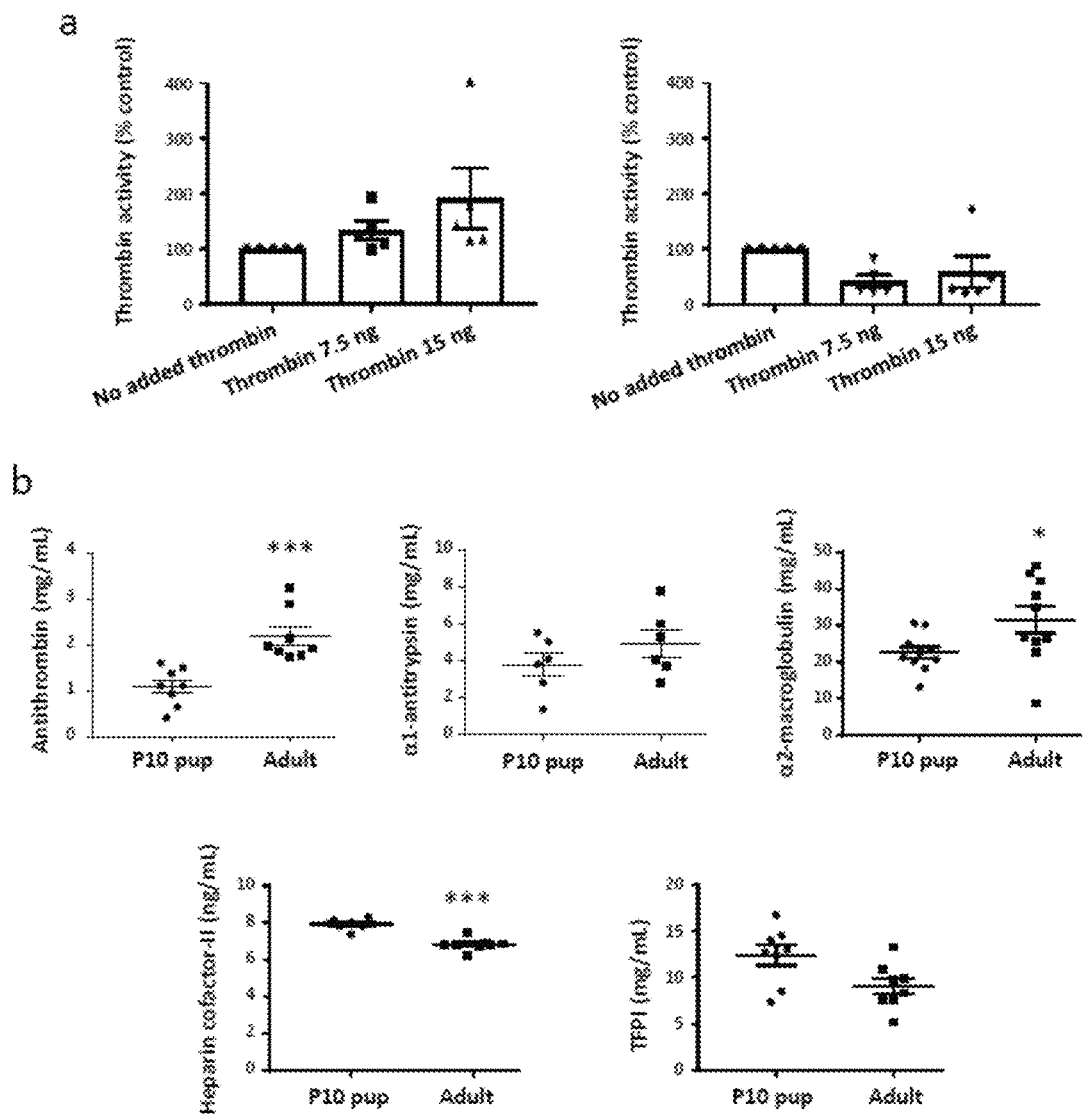
FIGS. 4A and 4B. Regulators of thrombin activity in pups and adult plasma.

Human neonates have a developmental antithrombotic deficiency, which may be accentuated during critical illness and may potentiate the effects of thrombin generated during tissue injury. [Manco-Johnson M J. Neonatal antithrombotic III deficiency. *Am J Med.* 1989; 87(3B):49S-52S.] To determine whether neonatal mice are also deficient in these endogenous thrombin antagonists, plasma from P10 pups and adult mice was spiked with increasing amounts of recombinant thrombin and measured thrombin activity after each addition. Addition of recombinant thrombin increased thrombin activity in neonatal plasma in a dose-dependent fashion, but produced no change in adult plasma (FIG. 4a). These findings were consistent with a developmental deficiency of endogenous thrombin antagonists in pups. In terms of specific antagonists, pups had lower antithrombotic and α2-macroglobulin levels, comparable plasma concentrations of α1-antitrypsin and tissue factor-pathway inhibitor, and slightly higher levels in pups of heparin cofactor-II, which is a glycosaminoglycan-activated, minor inhibitor of thrombin. [O'Keeffe D, et al. The heparin binding properties of heparin cofactor II suggest an antithrombotic-like activation mechanism. *J Biol Chem.* 2004; 279(48):50267-50273; Tollefsen D M. Heparin cofactor II deficiency. *Arch Pathol Lab Med.* 2002; 126(11):1394-1400; Golino P. The inhibitors of the tissue factor:factor VII pathway. *Thromb Res.* 2002; 106(3):V257-265.]

Figures 5A, 5B, 5C, 5D, 5E, 5F:
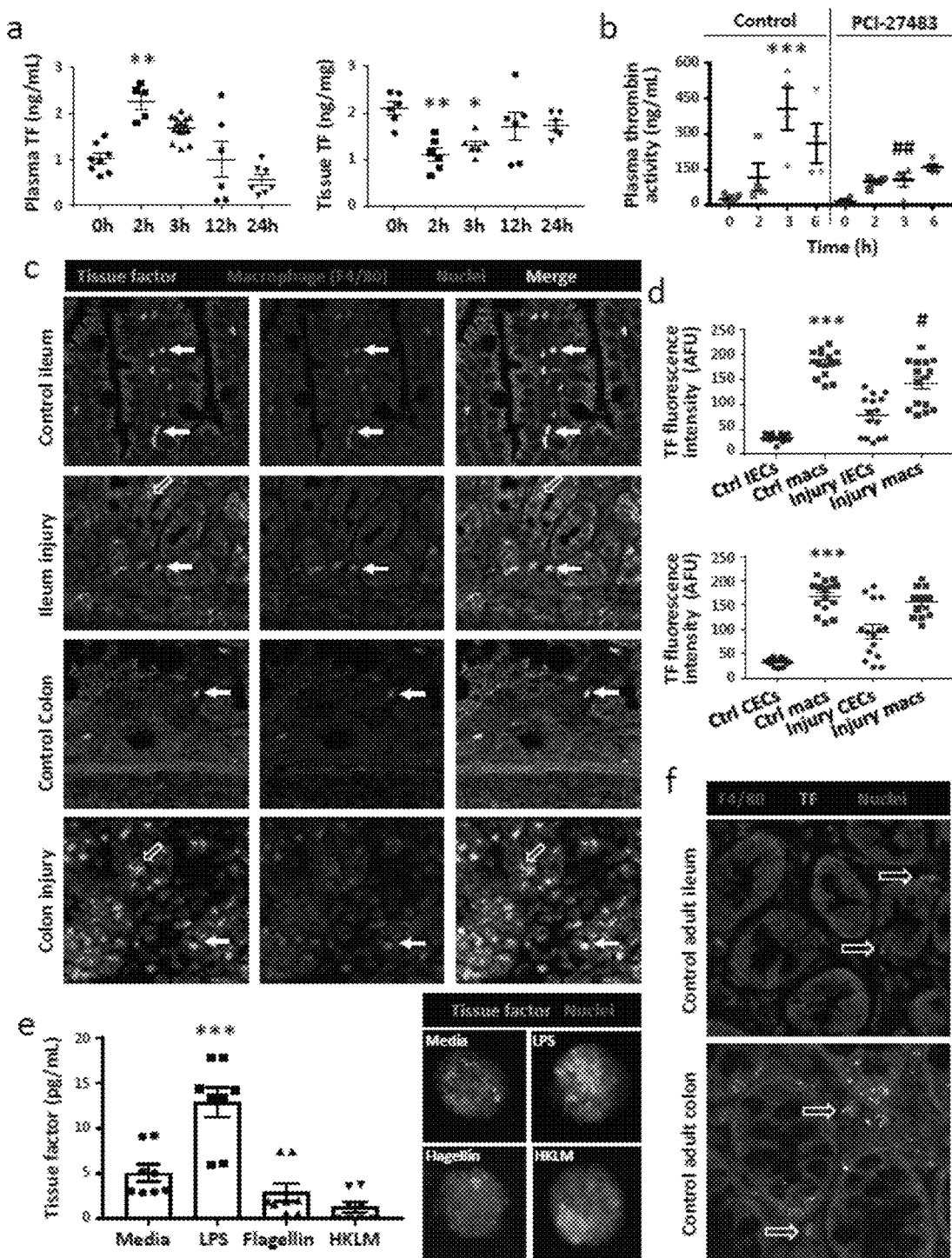
FIGS. 5A-5F. Resident intestinal macrophages release tissue factor to activate thrombin during neonatal intestinal injury.

Example 5. Intestinal Macrophages Release Tissue Factor to Activate Thrombin During Neonatal Intestinal Injury To investigate the mechanisms for thrombin activation, tissue factor (TF) concentrations were evaluated during NEC-like intestinal injury. Plasma TF was elevated at 2 h, preceding the rise in thrombin activity at 3 h. An inverted change with a transient drop in TF levels was seen in intestinal tissue at these time-points (tissues obtained from different animals) indicating that pre-formed TF stores can have been released from the intestine during bowel injury (FIG. 5a). To determine the pathophysiological contribution of tissue factor in neonatal intestinal injury, some mice were treated with PCI-27483, which inhibits factor VIIa in the VIIa/TF complex, [Gomez-Outes A, et al. New parenteral anticoagulants in development. *Ther Adv Cardiovasc Dis.* 2011; 5(1):33-59] before subjecting these animals to intestinal injury. Pre-treatment with PCI-27483 blocked the rise in plasma thrombin activity during intestinal injury (FIG. 5b).

Figures 15A, 15B:
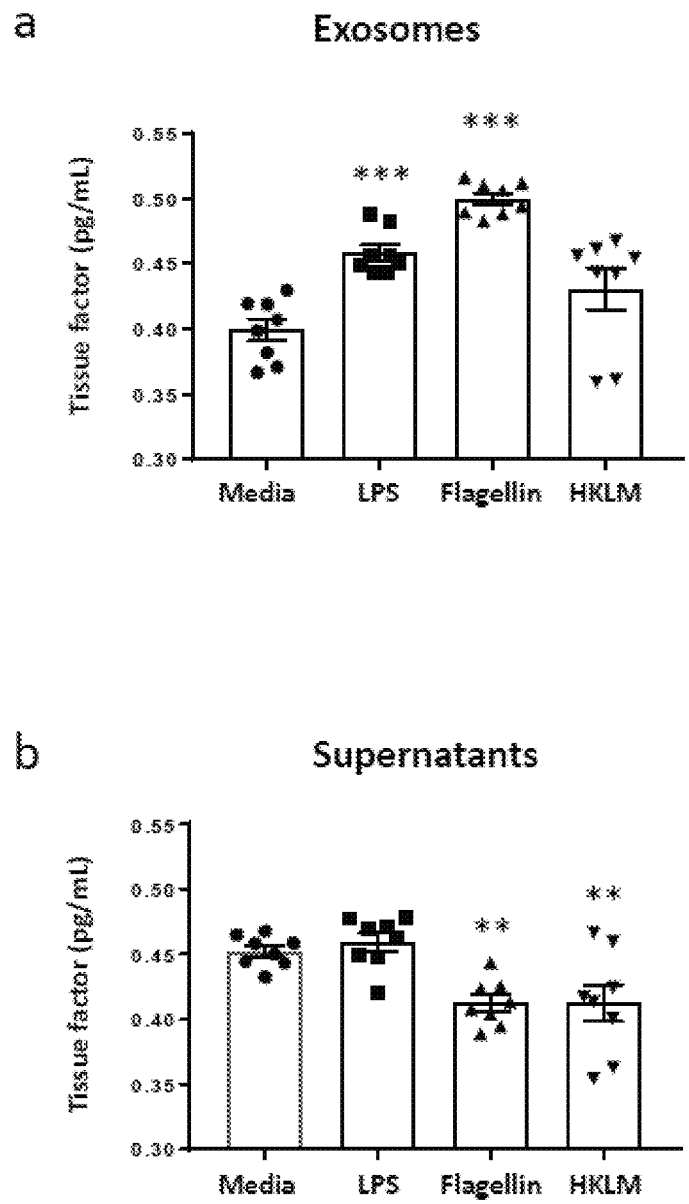
FIGS. 15A and 15B. Scatter bar diagrams (means±SEM) summarize tissue factor released from F4/80+ resident intestinal macrophages into (A) exosomal, and (B) supernatant fractions. Data show TF concentrations, measured by enzyme immunoassay (pg/mL). N=8 replicates/group; 3 mice. Kruskal Wallis H test with Dunn's post-test for group comparisons,  $P<0.01$, * $P<0.001$ vs. control.

Immunohistochemistry was used to identify the cellular sources of TF in the intestine. Strong TF immunoreactivity was detectable in F4/80+ intestinal macrophages in both control and intestinal injury. In the injured intestine, focal immunoreactivity for TF was also detected in some epithelial cells (FIGS. 5c and 5d). No subendothelial TF staining can be found in blood vessels [Drake T A, et al. Selective cellular expression of tissue factor in human tissues. Implications for disorders of hemostasis and thrombosis. *Am J Pathol.* 1989; 134(5):1087-1097] in the neonatal intestine. The intestinal macrophages were next isolated by immunomagnetic sorting [MohanKumar K, et al. Smad7 Interrupts TGF-β Signaling in Intestinal Macrophages and Promotes Inflammatory Activation of these Cells during Necrotizing Enterocolitis. *Pediatr Res.* 2016; 79(6):951-961] and examined for TF expression in vitro. Macrophages showed constitutive and LPS-induced secretion of TF, which was released mainly in microvesicles (FIG. 5e), not in exosomes or in the soluble fraction (FIGS. 15a and 15b). TF was immunolocalized in well-defined cytoplasmic compartments (0.1-0.25 μm diameter). Unlike intestinal macrophages in pups, macrophages in the adult mouse intestine did not express TF (FIG. 5f).

Example 6. Bivalirudin-Tagged Nanoparticles Protect Against Neonatal Intestinal Injury The generated data implicate a pathophysiological role of thrombin in neonatal intestinal injury. It is shown that bivalirudin blocked platelet in a pre-clinical model. While a few clinical studies have evaluated bivalirudin to inhibit thrombin activity in human infants, concerns remain about the risk of hemorrhagic complications. [Buck M L. Bivalirudin as an Alternative to Heparin for Anticoagulation in Infants and Children. *J Pediatr Pharmacol Ther.* 2015; 20(6):408-417.] Therefore, evaluation was done on antithrombotic nanoparticles (NPs) which can bind thrombin in nascent blood clots and prevent progressive activation of the coagulation cascades, and at least in preclinical models, have not increased the risk of systemic hemorrhagic complications. [Myerson J, He L, et al. Thrombin-inhibiting perfluorocarbon nanoparticles provide a novel strategy for the treatment and magnetic resonance imaging of acute thrombosis. *J Thromb Haemost.* 2011; 9(7):1292-1300.]

Figures 6A, 6B, 6C, 6D, 6E, 6F, 6G, 6H, 6I, 6J:
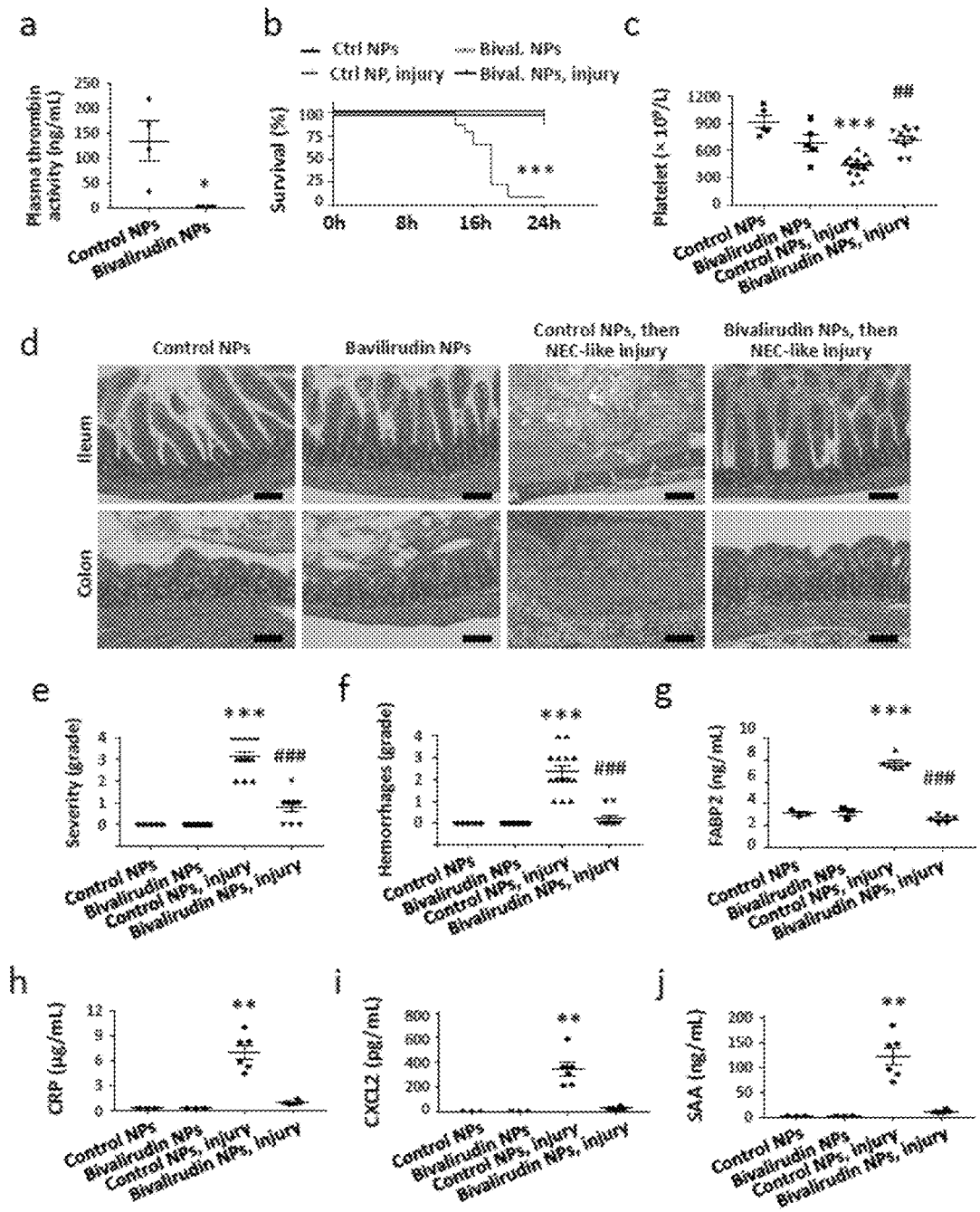
FIGS. 6A-6J. Bivalirudin-tagged nanoparticles protect against neonatal intestinal injury.

To confirm the activity of antithrombotic NPs in vivo, control and bivalirudin-tagged perfluorocarbon-core NPs were first administered in P10 mice at 3 h into the neonatal intestinal injury protocol (dose equivalent to $5.4 \times 10^8$ mol of bivalirudin/g body weight). As shown in FIG. 6a, Bivalirudin NPs completely inhibited plasma thrombin activity during intestinal injury.

Next, it was investigated whether bivalirudin-tagged NPs can prevent/ameliorate neonatal intestinal injury. Existing data indicate an in vivo half-life of ~4 h for these NPs, and therefore, NPs were administered at 1 h prior to TNBS administration and a $2^{nd}$ dose 4 h later. Bivalirudin NPs prevented mortality due to intestinal injury (FIG. 6b), prevented thrombocytopenia (FIG. 6c), and reduced the severity of intestinal injury (FIGS. 6d and 6e), without increasing hemorrhages into the injured intestine (FIG. 6f. Pups treated with bivalirudin NPs had lower plasma concentrations of FABP2 (FIG. 6g), which marks intestinal epithelial injury, and of the inflammatory markers C-reactive protein, CXCL2, and serum amyloid A (FIGS. 6h, 6i, and 6j).

Figures 16A, 16B:
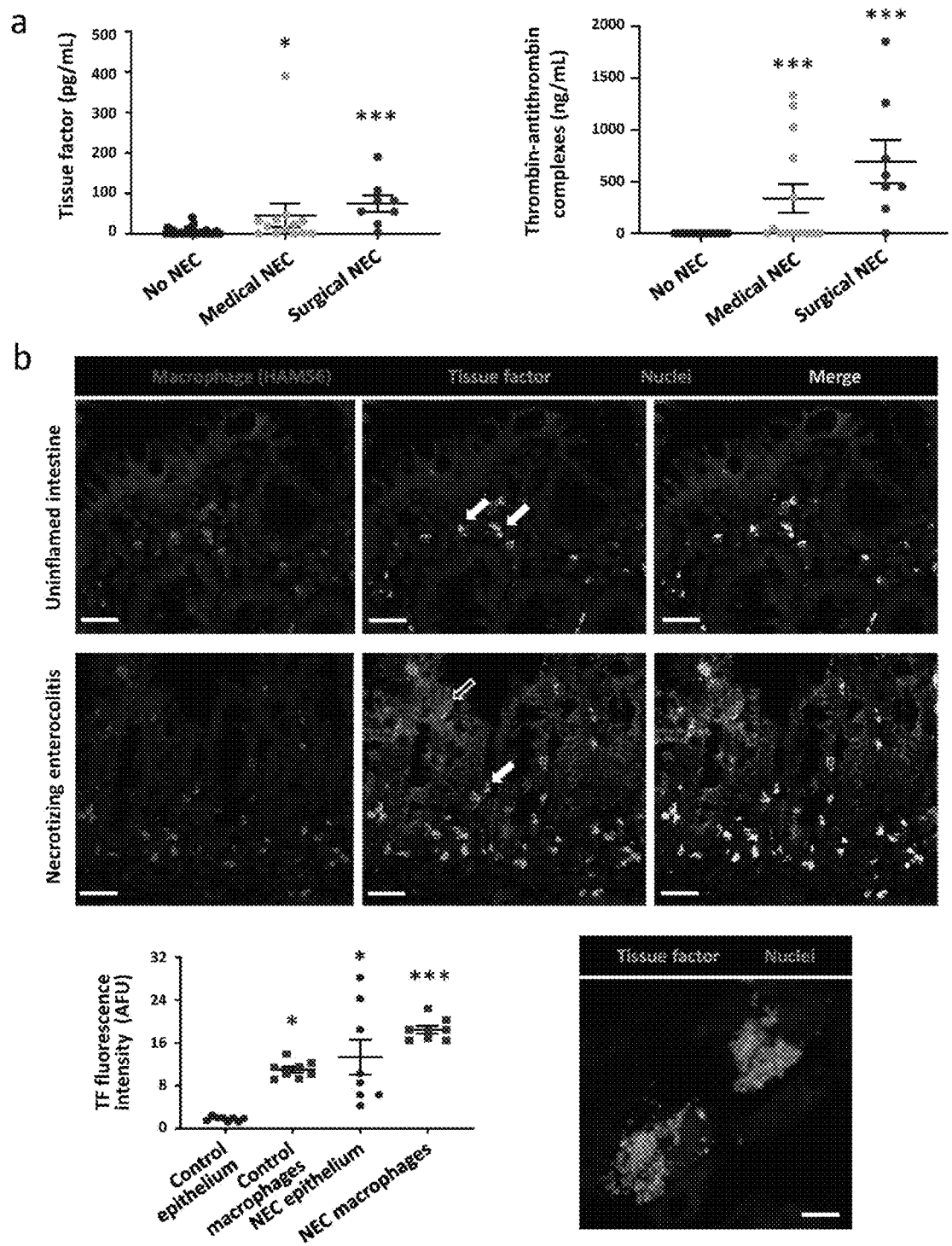
FIGS. 16A and 16B. Infants with NEC show increased circulating tissue factor and TAT complexes, and macrophages in the premature human intestine express tissue factor. (A) Scatterplots (means±SEM) summarize plasma concentrations of tissue factor (left) and thrombin-antithrombin complexes (right) in controls, patients with medical NEC, and in those with surgical NEC. NEC samples were drawn within 48 h of disease onset. N=22 patients, controls; Mann-Whitney U test, *** $P<0.001$ vs. control; (B) Representative fluorescence photomicrographs (magnification 200×) of uninflamed premature intestine (top) show immunoreactivity for TF (green) in intestinal macrophages (HAM56+, red). In the inflamed mucosa of NEC lesions (bottom), TF immunoreactivity was more extensive and was seen in macrophages, focally in epithelial cells (open arrow), and in some mesenchymal cells. Scale bar 20 μm. Scatter plots below summarize the fluorescence intensity for TF in the epithelium and macrophages in control and NEC intestine, respectively. N=8 patient samples/group; Kruskal Wallis H test with Dunn's post-test for group comparisons, * $P<0.05$, *** $P<0.001$. Bottom right: High magnification fluorescence photomicrograph (5400×) of intestinal macrophages shows TF staining localized to discrete cytoplasmic compartments. Scale bar 5 μm. N=8 patient samples.
Figure 17:
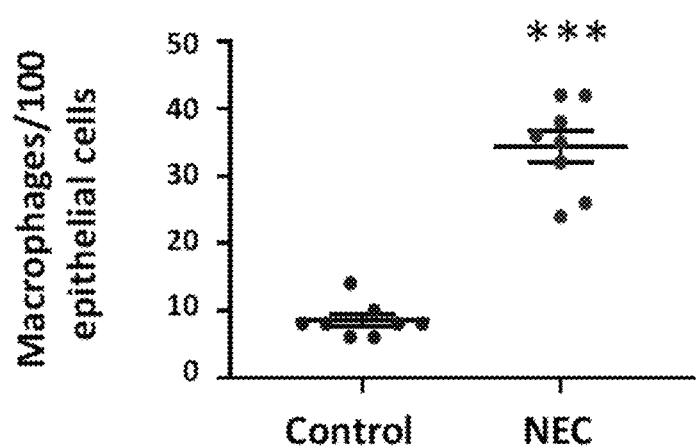
FIG. 17. Scatter bar diagram (means±SEM) summarizes the number of macrophages per 100 epithelial cells in control (uninflamed premature intestine) and tissue specimens of NEC. N=8 patient samples/group. Mann-Whitney U test, *** $P<0.001$.

Example 7. Infants with NEC Show Increased Circulating Tissue Factor and TAT Complexes, and Macrophages in the Premature Human Intestine Express Tissue Factor To confirm the findings in the mouse model, circulating concentrations of tissue factor and thrombin-antithrombin complexes were measured in patients with NEC (N=22). These patients were born at gestation 29.2±4.4 weeks with birth weight 1204±603 g, and blood samples were drawn on postnatal day 29.2±4.2, within 48 h of disease onset. In the comparison group, premature infants who did not have a diagnosis of NEC were included (N=40; gestational age 27.3±0.4 weeks, birth weight 1033±52 g; blood samples collected on postnatal day 21). Patients with NEC had elevated tissue factor and thrombin-antithrombin complexes, which increased with disease severity (FIG. 16a). To ascertain that macrophages in human neonatal intestine express tissue factor similar to murine neonatal macrophages, assessment was done on uninflamed premature intestine resected for intestinal obstruction secondary to reasons other than NEC (intestinal atresia 5, meconium plug 2, and congenital adhesions 1). Similar to the findings in murine pups, intestinal macrophages in the uninflamed premature intestine showed strong cytoplasmic immunoreactivity for tissue factor (FIG. 16b, solid arrows). These findings contrasted with the inflamed mucosa of NEC lesions, where tissue factor expression was no longer limited to macrophages, but was also seen focally in epithelial cells, and also in some pericryptal mesenchymal cells. Similar to murine intestinal injury, no perivascular tissue factor staining was seen (FIG. 16b). The macrophage infiltration noted in NEC lesions (FIG. 17) has been reported previously. (Remon J I, et al. Depth of bacterial invasion in resected intestinal tissue predicts mortality in surgical necrotizing enterocolitis. J Perinatol. 2015; 35(9):755-62.) Under higher magnification, macrophage tissue factor staining was localized to discrete cytoplasmic compartments similar (0.38±0.01 µm diameter) to murine neonatal intestinal macrophages (FIG. 5e). Taken together, these data confirm key findings from the murine model of NEC-like injury indicating an important pathophysiological role of macrophage-derived tissue factor and thrombin activation in human NEC.

Example 8. Platelet Activation and the Pathophysiological Effects Thereof for Treating Neonatal, Human NEC-Like Intestinal Injury Disclosed herein is a detailed investigation of platelet activation and its pathophysiological effects in the preclinical model of neonatal, human NEC-like intestinal injury. Platelet activation was anticipated to be a delayed, secondary consequence of mucosal damage and resulting bacterial translocation. Instead, platelet activation unexpectedly turned out to be an early, thrombin-mediated process and an important pathophysiological event during neonatal intestinal injury. Thrombin was identified as the primary activator of platelets, and to have potentiated effects in neonates because of the relative paucity of endogenous thrombin antagonists. Constitutive and LPS-inducible TF production was also detected in resident macrophages in the neonatal intestine. Finally, antithrombotic NPs are a novel, specific, and safe treatment for neonatal intestinal injury and the associated inflammatory response. Disclosed herein is the first study to identify platelet activation and thrombin as therapeutic targets for human NEC.

The protective effect of platelet depletion observed in the presently disclosed model of neonatal intestinal injury is intriguing. Thrombocytopenia occurs in most patients with confirmed NEC, [Hutter J J, Jr., et al. Hematologic abnormalities in severe neonatal necrotizing enterocolitis. J Pediatr 1976; 88(6):1026-1031; Kling P J, Hutter J J. Hematologic abnormalities in severe neonatal necrotizing enterocolitis: 25 years later. J Perinatol. 2003; 23(7):523-530; Maheshwari A. Immunologic and Hematological Abnormalities in Necrotizing Enterocolitis. Clin Perinatol. 2015; 42(3):567-585; Patel C C. Hematologic abnormalities in acute necrotizing enterocolitis. Pediatr Clin North Am. 1977; 24(3):579-584; Christensen R D, et al. Thrombocytosis and thrombocytopenia in the NICU: incidence, mechanisms and treatments. J Matern Fetal Neonatal Med. 2012; 25 Suppl 4:15-17; Ververidis M, et al. The clinical significance of thrombocytopenia in neonates with necrotizing enterocolitis. J Pediatr Surg. 2001; 36(5):799-803; Baer V L, et al. Do platelet transfusions in the NICU adversely affect survival? Analysis of 1600 thrombocytopenic neonates in a multihospital healthcare system. J Perinatol. 2007; 27(12):790-796; Gerday E, et al. Testing platelet mass versus platelet count to guide platelet transfusions in the neonatal intensive care unit. Transfusion. 2009; 49(10): 2034-2039; Baer V L, et al. Implementing a program to improve compliance with neonatal intensive care unit transfusion guidelines was accompanied by a reduction in transfusion rate: a pre-post analysis within a multihospital health care system. Transfusion. 2011; 51(2):264-269] and because premature infants are at risk of life-threatening hemorrhagic complications, [Stanworth S J, Clarke P, Watts T, et al. Prospective, observational study of outcomes in neonates with severe thrombocytopenia. Pediatrics. 2009; 124(5): e826-834] is treated aggressively with platelet transfusions to keep platelet counts above arbitrarily-assigned thresholds. [Josephson C D, et al. Platelet transfusion practices among neonatologists in the United States and Canada: results of a survey. Pediatrics. 2009; 123(1):278-285; Cremer M, et al. Platelet transfusions in neonates: practices in the United States vary significantly from those in Austria, Germany, and Switzerland. Transfusion. 2011; 51(12):2634-2641.] However, the possibility of harm from activated platelets, which release pre-formed vasoconstrictors and inflammatory mediators, is also highly plausible. [Collins C E, Cahill M R, Newland A C, Rampton D S. Platelets circulate in an activated state in inflammatory bowel disease. Gastroenterology. 1994; 106(4):840-845; Thomas M R, Storey R F. The role of platelets in inflammation. Thromb Haemost. 2015; 114(3):449-458.] There is some information linking multiple platelet transfusions with suboptimal outcomes in NEC, [Baer V L, et al. Do platelet transfusions in the NICU adversely affect survival? Analysis of 1600 thrombocytopenic neonates in a multihospital healthcare system. J Perinatol. 2007; 27(12):790-796; Kenton A B, et al. Platelet transfusions in infants with necrotizing enterocolitis do not lower mortality but may increase morbidity. J Perinatol. 2005; 25(3):173-177; Garcia M G, et al. Epidemiologic and outcome studies of patients who received platelet transfusions in the neonatal intensive care unit. J Perinatol. 2001;

21(7):415-420] but most clinicians continue to use liberal transfusion thresholds in these infants because it is unclear whether the inferior outcomes in infants receiving platelet transfusions reflect harm from transfused platelets or merely the confounding effect of higher severity of illness. [Josephson C D, et al. Platelet transfusion practices among neonatologists in the United States and Canada: results of a survey. *Pediatrics*. 2009; 123(1):278-285; Cremer M, et al. Platelet transfusions in neonates: practices in the United States vary significantly from those in Austria, Germany, and Switzerland. *Transfusion*. 2011; 51(12):2634-2641.] In a recent study, preterm infants with severe thrombocytopenia had higher mortality or major bleeding when they received platelet transfusion(s) at a platelet-count threshold of <50× $10^9$/L than those transfused at platelet counts<25×$10^9$/L.[42] The data disclosed herein also support the idea that that low platelet counts do not always need prompt correction, and call for re-evaluation of platelet transfusion guidelines in premature infants.

Thrombin was identified as the primary mechanism for platelet activation during NEC-like intestinal injury. LPS, txA2, and PAF were evaluated as alternative mechanisms, but only increased thrombin activity (and increased thrombin-antithrombotic complexes) antedated platelet activation. The relative paucity of antithrombotic can potentiate the biological effects of thrombin in neonates and add credence to the role of thrombin in NEC pathogenesis. Thrombin accumulation and thrombin-mediated platelet activation are important mechanisms for recruiting platelets into a growing hemostatic plug and can be an early event during DIC. However, in the model disclosed herein, thrombin generation was independent of major tissue disruption or DIC markers such as FDPs, indicating that thrombin generation can be a primary event unrelated to clot formation. This is the first report to identify thrombin generation as a pathophysiological event in intestinal injury. Modest elevations in thrombin generation have been noted in patients with active ulcerative colitis and Crohn's disease, but thrombin is viewed as a secondary mediator of inflammation and a predictor of thrombotic events in these conditions. [Saibeni S, et al. Increased thrombin generation in inflammatory bowel diseases. *Thromb Res*. 2010; 125(3):278-282; Deutschmann A, et al. Increased procoagulant function of microparticles in pediatric inflammatory bowel disease: role in thrombin generation. *J Pediatr Gastroenterol Nutr*. 2013; 56(4): 401-407.]

The detection of pre-formed tissue factor (TF) in resident macrophages in the neonatal intestine is novel. TF is a 30-kDa transmembrane glycoprotein that is expressed on subendothelial smooth muscle, epithelia, circulating leukocytes, and platelets. [Drake T A, et al. Selective cellular expression of tissue factor in human tissues. Implications for disorders of hemostasis and thrombosis. *Am J Pathol*. 1989; 134(5):1087-1097; Chen J, et al. Antithrombotic nanoparticles improve kidney reperfusion and protect kidney function after ischemia-reperfusion injury. *Am J Physiol Renal Physiol*. 2015; 308(7): F765-773.] Consistent with data in adult mice, resident macrophages in the adult human gastrointestinal tract are also known to not express TF. [Drake T A, et al. Selective cellular expression of tissue factor in human tissues. Implications for disorders of hemostasis and thrombosis. *Am J Pathol*. 1989; 134(5):1087-1097.] In the vascular compartment, TF is believed to provide a protective hemostatic envelope; if the vessel wall is injured due to any reason, subendothelial TF is exposed and becomes available to complex with circulating factor VII, activating coagulation cascades that eventually lead to thrombin generation. [Zelaya H, et al. Tissue factor at the crossroad of coagulation and cell signaling. *J Thromb Haemost*. 2018; 16(10):1941-1952.] The role of TF expressed on leukocytes and platelets is less well understood. In the neonatal intestine, no perivascular TF expression was detected but evidence for constitutive and inducible TF secretion by macrophages was found. LPS-induced macrophage TF expression is also of interest in view of increasing information linking NEC with bacterial overgrowth and enteric dysbiosis with enrichment of Gram-negative bacteria. [Pammi M, et al. Intestinal dysbiosis in preterm infants preceding necrotizing enterocolitis: a systematic review and meta-analysis. *Microbiome*. 2017; 5(1):31.] Another aspect of macrophage TF expression was localization in well-defined cytoplasmic compartments, and at least in ex vivo studies, these macrophages released TF specifically into microvesicles.

The current disclosure shows the use of antithrombotic NPs to prevent/ameliorate NEC-like injury. These findings are particularly exciting because no effective treatments are currently available for NEC, with clinical management limited to supportive measures and surgical resection of the necrosed bowel. Needless to say, NEC continues to be associated with mortality rates of 25-40% despite major improvements in neonatal intensive care and reduction in all-cause mortality in premature infants. [Patel R M, et al. Causes and timing of death in extremely premature infants from 2000 through 2011. *N Engl J Med*. 2015; 372(4):331-340.] The disclosed data show that nanomedicine approaches offer a therapeutic platform for clinical evaluation. Targeted nanomedicine allows high drug concentrations in the intended local environments while the total drug concentration and side effects are significantly reduced. Perfluorocarbon (PFC) NPs (~250 nm) can be formulated by conjugating bivalirudin to a perfluorooctylbromide core. [Chen J, et al. Antithrombotic nanoparticles improve kidney reperfusion and protect kidney function after ischemia-reperfusion injury. *Am J Physiol Renal Physiol*. 2015; 308(7):F765-773.] Compared with other nanomedicine platforms, these PFC NPs have several unique advantages as therapeutic agents. First, PFC nanoparticles are not dependent on renal function for clearance. [Wickline S A, et al. Applications of nanotechnology to atherosclerosis, thrombosis, and vascular biology. *Arterioscler Thromb Vasc Biol*. 2006; 26(3):435-441.] These NPs are cleared from the circulation by the reticuloendothelial system and the perfluorocarbon component is ultimately vaporized through the lung. [Chen J, et al. Quantitative magnetic resonance fluorine imaging: today and tomorrow. *Wiley Interdiscip Rev Nanomed Nanobiotechnol*. 2010; 2(4):431-440.] Second, the PFC core permits quantitative molecular imaging with fluorine magnetic resonance in vivo, which may allow assessment of regional seeding, thrombin binding, and the outcomes of bowel necrosis and injury.

In conclusion, the current disclosure shows that thrombin-mediated platelet activation is an early, key pathophysiological event during neonatal intestinal injury. Thus, disclosed herein are methods of treating necrotizing enterocolitis using an antithrombotic nanoparticle comprising a thrombin inhibitor.

Example 8. Materials and Methods

Murine studies: Animal studies were approved by the Institutional Animal Care and Use Committees at the University of South Florida and Johns Hopkins University. Mice were procured from Jackson Labs (Bar Harbor, Me.). C57BL/6-Tg (Pf4-icre) Q3Rsko/J (Jax stock #008535) and B6.129X1-Gt (ROSA) 26Sor$^{tm1\ (EYFP)\ Cos}$/J (stock #006148) have been described previously. [Srinivas S, et al. Cre reporter strains produced by targeted insertion of EYFP and ECFP into the ROSA26 locus. *BMC Dev Biol.* 2001; 1:4; Tiedt R, et al. Pf4-Cre transgenic mice allow the generation of lineage-restricted gene knockouts for studying megakaryocyte and platelet function in vivo. *Blood.* 2007; 109 (4):1503-1506.]

NEC-like injury was induced on P10 by administering TNBS (2 doses of 50 mg/kg in 30% ethanol, w/v; Sigma, St. Louis, Mo.) by gavage and rectal instillation, respectively. [Namachivayam K, et al. Neonatal Mice with Necrotizing Enterocolitis-like Injury Develop Thrombocytopenia despite Increased Megakaryopoiesis. *Pediatr Res.* 2017; 81:817-824; MohanKumar K, et al. Gut mucosal injury in neonates is marked by macrophage infiltration in contrast to pleomorphic infiltrates in adult: evidence from an animal model. *Am J Physiol Gastrointest Liver Physiol.* 2012; 303(1):G93-102; MohanKumar K, et al. Trinitrobenzene Sulfonic Acid-induced Intestinal Injury in Neonatal Mice Activates Transcriptional Networks Similar to those seen in Human Necrotizing Enterocolitis. *Pediatr Res.* 2016; 81(1):99-112; MohanKumar K, et al. Smad7 Interrupts TGF-β Signaling in Intestinal Macrophages and Promotes Inflammatory Activation of these Cells during Necrotizing Enterocolitis. *Pediatr Res.* 2016; 79(6):951-961.] Controls received vehicle alone. Some pups were rendered thrombocytopenic ($50\text{-}100\times10^9$/L) by intraperitoneal 0.05 μg anti-GP1bα per g body weight (Emfret Analytics, Eibelstadt, Germany) 12 h before TNBS. Animals were monitored every 3 h and were euthanized at onset of illness or at 48 h using $CO_2$ inhalation followed by cervical dislocation. Histopathological grading of intestinal injury has been previously described [MohanKumar K, Kaza N, Jagadeeswaran R, et al. Gut mucosal injury in neonates is marked by macrophage infiltration in contrast to pleomorphic infiltrates in adult: evidence from an animal model. *Am J Physiol Gastrointest Liver Physiol.* 2012; 303 (1): G93-102]: grade 0=no injury; grade 1=mild injury; disruption of villus tips or mild separation of *Lamina propria* in ileum; leukocyte infiltration in colon in <10% high-power fields (HPF); no structural changes; grade 2=moderate injury; mid-villus disruption, clear separation of *Lamina propria* and/or submucosal edema in ileum; prominent leukocyte infiltration in colon in ≤50% HPF, crypt elongation, mucosal thickening, superficial ulcerations; grade 3=severe injury: transmural injury in ileum; marked leukocyte infiltration in >50% HPF, elongated and distorted crypts, bowel-wall thickening, and extensive ulcerations.

Platelet Isolation and Measurements: Platelets were isolated using established methods. (Sorensen A L, et al. Role of sialic acid for platelet life span: exposure of beta-galactose results in the rapid clearance of platelets from the circulation by asialoglycoprotein receptor-expressing liver macrophages and hepatocytes. *Blood.* 2009; 114(8):1645-1654.) Blood was collected by anterior facial vein puncture or at sacrifice using a 25G needle on a syringe containing 1 vol ACD for 6 vol blood. Red cells and leukocytes were removed by centrifugation at 300×g (6 min/no brake/22° C.), and then platelet-rich plasma was prepared by centrifugation at 2200×g (10 min/no brake/22° C.). Platelets were resuspended in HEPES Tyrode's albumin buffer (TAB) containing heparin (10 U/mL) and ILoprost (0.5 μM, Sigma) at 37° C.×10 min, and then resuspended in TAB containing 0.02 U/mL aprase ($1\text{-}3\times10^5$/μL; Sigma). To minimize inadvertent effects of blood loss on intestinal injury and platelet kinetics, each animal was subjected to a maximum of 3-4 phlebotomies. Platelet counts were measured using a Sysmex XT-2000iV hematology analyzer. [Namachivayam K, et al. Neonatal Mice with Necrotizing Enterocolitis-like Injury Develop Thrombocytopenia despite Increased Megakaryopoiesis. *Pediatr Res.* 2017; 81:817-824; Liu Z J, et al. Expansion of the neonatal platelet mass is achieved via an extension of platelet lifespan. *Blood.* 2014; 123(22):3381-3389.]

Platelet activation markers were measured by flow cytometry, using the following fluorescence-labeled antibodies: JON/A (Emfret); anti-CD62P, anti-CD41/GPIIb, CD61/integrin αvβ3, CD31/PECAM-1 (BioLegend, San Diego, Calif.). Platelets were evaluated by size-gate threshold adjustment with microbeads of known diameter (100 nm to 1.3 μm; Spherotech, Lake Forest, Ill.) in forward and side-scatter. [Nielsen M H, et al. A flow cytometric method for characterization of circulating cell-derived microparticles in plasma. *J Extracell Vesicles.* 2014; 3.] Platelet aggregation was measured by impedance method and ATP release by luminometry using a 2-channel Chrono-Log lumi-aggregometer (model 700, Chrono-Log, Havertown, Pa., USA) per established methods. [Novak E K, et al. Cocoa: anew mouse model for platelet storage pool deficiency. *Br J Haematol.* 1988; 69(3):371-378.]

Dense granules were stained with mepacrine (Quinacrine dihydrochloride; Sigma). Mepacrine was dissolved in DMSO, diluted in Hanks balanced salt solution (0.5 mM), warmed at 37° C. until it became transparent, and then stored in aliquots at 4° C. For staining, blood was diluted 1:40 in HEPES buffer, incubated ×10 min, and then incubated with mepacrine solution (final concentration 65 μmol/L)×30 min in dark at 37° C. Platelets were washed twice and resuspended in HEPES TAB. Fluorescence was measured at 436/525 nm.

For transmission electron microscopy, platelets were fixed with glutaraldehyde (Sigma), treated with osmic acid and dehydrated in graded acetones before embedding in Epon-Araldite. Thin sections were examined with a JEOL JEM-1011 electron microscope. Details provided in the online supplement.

Quantitative protein measurements: Commercially-available enzyme immunoassays were used to measure murine FABP2, CXCL2, CRP, SAA, txA2, PAF, α2-macroglobulin, heparin cofactor-II, F3/tissue factor, tissue factor pathway inhibitor, TAT complexes, fibrin degradation products (MyBioSource, San Diego, Calif.); antithrombin, and al-antitrypsin (Innovative Research, Novi, Mich.). Thrombin activity was measured by a fluorometric assay (Thrombin Activity Assay Kit, Abcam, Cambridge, Mass.), and the ADP/ATP ratio using a luciferase assay (ADP/ATP Ratio Assay Kit, Sigma). Plasma endotoxin levels were quantified by the Limulus Amebocyte Lysate assay (ThermoFisher Scientific, Waltham, Mass.).

Chemicals: Recombinant mouse thrombin (Molecular Innovations, Novi, Mich.), PAF (Cayman Chemicals, Ann Arbor, Mich.), PPACK dihydrochloride (SCBT, Santa Cruz, Calif.), bivalirudin trifluoroacetate (Sigma).

Immunofluorescence imaging: The previously-described immunofluorescence protocols [MohanKumar K, et al. Smad7 Interrupts TGF-β Signaling in Intestinal Macrophages and Promotes Inflammatory Activation of these Cells during Necrotizing Enterocolitis. *Pediatr Res.* 2016; 79(6): 951-961; Namachivayam K, et al. Smad7 inhibits autocrine expression of TGF-beta2 in intestinal epithelial cells in baboon necrotizing enterocolitis. *Am J Physiol Gastrointest Liver Physiol.* 2013; 304(2):G167-180] were used to stain murine cells and tissues for macrophage marker F4/80 and tissue factor.

Murine intestinal macrophages isolation. Intestinal macrophages were isolated by immunomagnetic separation as previously described (details in online supplement)[16] and treated in vitro with LPS (*E. coli* K12), Flagellin from *S. typhimurium*, and HKLM (Heat-killed *Listeria monocytogenes*; Invivogen, San Diego, Calif.). Culture supernatants were fractionated to first separate microvesicles by centrifugation at 20,000×g for 40 min at RT (Sorvall WX ultracentrifuge, ThermoFisher) and then exosomes by another centrifugation at 100,000×g for 1 h at 4° C. [Aatonen M T, et al. Isolation and characterization of platelet-derived extracellular vesicles. *J Extracell Vesicles*. 2014; 3.]

PFC NPs: PFC NPs were formulated with PFOB emulsion 20% (v/v; Exfluor Research, Round Rock, Tex.), 2% (w/v) of a surfactant commixture, and 1.7% (w/v) glycerin, and then conjugated with bivalirudin. [Myerson J, et al. Thrombin-inhibiting perfluorocarbon nanoparticles provide a novel strategy for the treatment and magnetic resonance imaging of acute thrombosis. *J Thromb Haemost*. 2011; 9(7):1292-1300; Chen J, et al. Antithrombotic nanoparticles improve kidney reperfusion and protect kidney function after ischemia-reperfusion injury. *Am J Physiol Renal Physiol*. 2015; 308(7):F765-773; Wickline S A, et al. Applications of nanotechnology to atherosclerosis, thrombosis, and vascular biology. *Arterioscler Thromb Vasc Biol*. 2006; 26(3):435-441; Chen J, et al. Quantitative magnetic resonance fluorine imaging: today and tomorrow. *Wiley Interdiscip Rev Nanomed Nanobiotechnol*. 2010; 2(4):431-440.] These NPs had an average diameter of 269.8 nm, polydispersity of 0.146, and zeta potential of −20 mV.

Transfusion of YFP$^+$ platelets: YFP$^+$ platelets were harvested from PF-4 cre mice×R26-stop-YFP mutant mice, and 1×10$^8$ platelets were transfused intravenously in wild type P10 mice with intestinal injury at 3 h.

Platelet counts: Blood obtained from the anterior facial vein (as described above) was collected using pipette tips and eppendorf tubes flushed with acid-citrate-dextrose buffer (Sigma); 5 µL blood was gently mixed with 95 µL Cellpack reagent (Sysmex Corp., Kobe, Japan) and platelet counts and indices were measured using an XT-2000iV automated veterinary hematology analyzer (Sysmex). This analyzer produces reproducible measurements with blood samples diluted 1:20. (Cremer M, et al. Platelet transfusions in neonates: practices in the United States vary significantly from those in Austria, Germany, and Switzerland. *Transfusion*. 2011; 51(12):2634-41.) To avoid inadvertent effects of blood loss on intestinal injury and platelet kinetics, each animal was subjected to a maximum of 3-4 phlebotomies.

Transmission electron microscopy of platelets. Platelet were fixed by incubating ×15 min with an equal volume of 0.1% glutaraldehyde (Sigma) in White's saline (10% solution of a 1:1 mixture of (a) 2.4 mM NaCl, 0.1 mM KCl, 46 mM MgSO4, and 64 mM Ca (NO3)2 4H2O and (b) 0.13 M NaHCO$_3$, 8.4 mM NaH2PO4, and 0.1 g/L of phenol red, pH 7.4). Samples were centrifuged and the pellets were resuspended in 3% glutaraldehyde in White's saline, maintained at 4° C. overnight. After centrifugation, the supernatant was removed and replaced with either 1% osmic acid in Zetterquist's buffer or 1% osmic acid in distilled water containing 1.5% potassium ferrocyanide×1 h at 4° C. and dehydrated in graded acetones before embedding in Epon-Araldite. Thin sections cut from the plastic blocks on an ultra-microtome were examined unstained or after staining with uranyl acetate and lead citrate to enhance contrast. For dense granule evaluation, unfixed platelets in a drop of PRP will be allowed to adhere to formvar-coated grids×5 min, fixed×1 min with a drop of 0.5% glutaraldehyde/PBS, dip rinsed in distilled water, and then blotted dry. Grids were examined with a JEOL JEM-1011 electron microscope and images were captured with a side-mounted Advantage HR CCD camera (Advanced Microscopy Technique, Danvers, Mass.).

Intestinal macrophages. Murine intestinal macrophages were isolated by immunomagnetic separation as previously described. (Neu J, and Walker W A. Necrotizing enterocolitis. *N Engl J Med*. 2011; 364(3):255-64.) Briefly, intestinal tissue was digested with HBSS containing 1 mM collagenase type IV (ThermoFisher)×2 h at 37° C. Macrophages were first stained with biotinylated anti-F4/80 antibodies and then separated using anti-biotin-conjugated ferromagnetic beads (Miltenyi Biotec, Gaithersburg, Md.). More than 90% of these cells were confirmed as F4/80+ macrophages by FACS. These isolated macrophages were cultured (RPMI with 10% FCS 1% antibiotics, 5% CO$_2$ at 37° C.) and treated in vitro with LPS (from *E. coli* K12), FLA-ST (Flagellin from *S. typhimurium*) and HKLM (Heat-killed preparation of *Listeria monocytogenes*; Invivogen, San Diego, Calif.).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will appreciate that numerous changes and modifications can be made to the preferred embodiments of the invention and that such changes and modifications can be made without departing from the spirit of the invention. It is, therefore, intended that the appended claims cover all such equivalent variations as fall within the true spirit and scope of the invention.

What is claimed is:

1. A method of treating necrotizing enterocolitis in a subject in need thereof, comprising administering to the subject a therapeutically effective amount of an antithrombotic nanoparticle comprising: a thrombin inhibitor, a vitamin K antagonist, synthetic pentasaccharide inhibitor of factor Xa, directly acting oral anticoagulant, direct factor Xa inhibitor, or a protease-activated receptor-1 (PAR-1) antagonist.

2. The method of claim 1, wherein the thrombin inhibitor comprises bivalirudin, hirudin, lepirudin, argatroban, dabigatran, ximelagatran, or D-phenylalanyl-N-[(1S)-4-[(aminoiminomethyl)amino]-1-(2-chloroacetyl)butyl]-L-prolinamide, trifluoroacetate salt (PPACK).

3. The method of claim 1, wherein the antithrombotic nanoparticle comprises a core and an outer layer.

4. The method of claim 3, wherein the outer layer comprises the thrombin inhibitor.

5. The method of claim 3, wherein the core comprises perfluorocarbon.

6. The method of claim 1, wherein the antithrombotic nanoparticle has a size ranging from about 1 nm to about 1000 nm.

7. The method of claim 6, wherein the antithrombotic nanoparticle has a size ranging from about 50 nm to about 1000 nm.

8. The method of claim 7, wherein the antithrombotic nanoparticle has a size about 250 nm.

9. The method of claim 1, wherein the antithrombotic nanoparticle further comprises an antiplatelet agent.

10. The method of claim 9, wherein the antiplatelet agent is selected from a cyclooxygenase inhibitor, an adenosine diphosphate (ADP) receptor inhibitor, a glycoprotein IIB/IIIA inhibitor, a thromboxane inhibitor, a thromboxane synthase inhibitor, or a thromboxane receptor antagonist.

11. The method of claim 3, wherein the outer layer of the antithrombotic nanoparticle further comprises a ligand that targets a cell that is activated by thrombin via PAR-1 receptors.

12. The method of claim 3, wherein the outer layer of the antithrombotic nanoparticle further comprises a ligand that targets an intestinal endothelial cell.

13. The method of claim 1, wherein the antithrombotic nanoparticle inhibits platelet activation.

14. The method of claim 1, wherein the administration of the antithrombotic nanoparticle decreases a level of tissue factor (TF).

15. The method of claim 1, wherein the administration of the antithrombotic nanoparticle decreases intestinal damage.

16. The method of claim 1, wherein the antithrombotic nanoparticle is comprised in an injectable dosage form.

17. The method of claim 1, wherein the half-life of the antithrombotic nanoparticle after a single intravenous bolus is between about 2 and about 4 hours.

* * * * *

SEQUENCE LISTING

<160> NUMBER OF SEQ ID NOS: 1

<210> SEQ ID NO 1
<211> LENGTH: 20
<212> TYPE: PRT
<213> ORGANISM: Artificial Sequence
<220> FEATURE:
<223> OTHER INFORMATION: SYNTHETIC CONSTRUCT

```
<220> FEATURE:
<221> NAME/KEY: D-amino acid
<222> LOCATION: (1)..(1)

<400> SEQUENCE: 1

Phe Pro Arg Pro Gly Gly Gly Gly Asn Gly Asp Phe Glu Glu Ile Pro
1               5                   10                  15

Glu Glu Tyr Leu
            20
```